US008821876B2

(12) United States Patent
Ginsburg et al.

(10) Patent No.: US 8,821,876 B2
(45) Date of Patent: Sep. 2, 2014

(54) METHODS OF IDENTIFYING INFECTIOUS DISEASE AND ASSAYS FOR IDENTIFYING INFECTIOUS DISEASE

(75) Inventors: Geoffrey S. Ginsburg, Durham, NC (US); Joseph Lucas, Chapel Hill, NC (US); Christopher W. Woods, Durham, NC (US); Lawrence Carin, Durham, NC (US); Aimee K. Zaas, Chapel Hill, NC (US); Alfred Hero, Ann Arbor, MI (US)

(73) Assignee: Duke University, Durham, NC (US)

( * ) Notice: Subject to any disclaimer, the term of this patent is extended or adjusted under 35 U.S.C. 154(b) by 182 days.

(21) Appl. No.: 13/322,232

(22) PCT Filed: May 26, 2010

(86) PCT No.: PCT/US2010/036257
§ 371 (c)(1),
(2), (4) Date: Nov. 23, 2011

(87) PCT Pub. No.: WO2011/008349
PCT Pub. Date: Jan. 20, 2011

(65) Prior Publication Data
US 2012/0114661 A1 May 10, 2012

Related U.S. Application Data

(60) Provisional application No. 61/181,216, filed on May 26, 2009.

(51) Int. Cl.
*A61K 39/42* (2006.01)
*C40B 30/00* (2006.01)

(52) U.S. Cl.
USPC ............. 424/147.1; 514/535; 514/459; 435/5

(58) Field of Classification Search
CPC ................................ C12Q 1/6883; A61K 6/00
See application file for complete search history.

(56) References Cited

U.S. PATENT DOCUMENTS

2009/0155180 A1  6/2009  Jump et al.

OTHER PUBLICATIONS

Fjaerli et al. (BMC, 2006, p. 1-7 in IDS on Jul. 12, 2013).*
Zaas et al. (Supplemental Data, Sep. 2009.*
Acharya CR, Hsu DS, Anders CK, et al. "Gene expression signatures, clinicopathological features, and individualized therapy in breast cancer." Jama 2008, 299:1574-1587.
Arruda E, Pitkaranta A, Witek TJ, Jr., et al., "Frequency and natural history of rhinovirus infections in adults during autumn." J Clin Microbial 1997, 35:2864-2868.
Aziz H, Zaas A, Ginsburg GS, "Peripheral blood gene expression profiling for cardiovascular disease assessment." Genomic Med 2007, 1: 105-112.

Barrett B, Brown R, Voland R, et al., "Relations among questionnaire and laboratory measures of rhinovirus infection." Eur Respir J 2006, 28:358-363.
Bassetti M, Righi E, Tumbarello M, et al., "*Candida* infections in the intensive care unit: epidemiology, risk factors and therapeutic strategies" Expert Rev Anti Infect Ther 2006, 4:875-885.
Berenguer J, Buck M, Witebsky F, et at., "Lysis-centrifugation blood cultnres in the detection of tissue-proven invasive candidiasis. Disseminated versus single organ infection" Diagn Microbiol Infect Dis 1993, 17: 103-109.
Bhoj VG, Sun Q, Bhoj EJ, et al., "MAVS and MyD88 are essential for innate immunity but not cytotoxic T lymphocyte response against respiratory syncytial virus." Proc Natl Acad Sci US A 2008, 105:14046-14051.
Boldrick JC, Alizadeh AA, Diehn M, et al., "Stereotyped and specific gene expression programs in human innate immune responses to bacteria." Proc Natl Acad Sci USA 2002, 99:972-977.
Breiman L, Friedman JH, Olshen LA, et al., "Classification and regression trees," Chapman and Hall/CRC; 1984.
Breiman L, "Statistical Modeling: The Two Cultures." Statistical Science 2001, 16:199-231.
Bryant PA, Venter D, Robins-Browne R, et al., "Chips with everything: DNA microarrays in infectious diseases." Lancet Infect Dis 2004, 4:100-111.
Cameron, C.M. et al., "Gene expression analysis of host innate immune responses during lethal H5N1 infection in ferrets," J. Virol. (2008) 29 pages.
Campbell and Ghazal, "Molecular signatures for diagnosis of infection: application of microarray technology," J Appl Microbial (2004) vol. 96, 18-23.
Carvalho C, Lucas J, Wang Q, et al., "High-dimensional sparse factor modeling: applications in gene expression genomics." Journal of the American Statistical Society 2008, in press.
Carvalho et al., "High dimensional sparse factor modeling: applications in gene expression genomics," Journal of American Statistical Association (2008) pp. 1-51.
Chiarini A, Palmeri A, Amato T, et al., "Detection of bacteria and yeast species by the BACTEC 9120 automated system with the routine use of aerobic, anaerobic, and fungal media." J Clin Microbial 2008, 4029-4033.
Chin KC, Cresswell P, "Viperin (cig5), an IFN-inducible antiviral protein directly induced by human cytomegalovirus." Proc Natl Acad Sci USA 2001 , 98:15125-15130.
Chipman H, George E, McCulloch RE, "Bayesian CART model search." Theory and Methods, No. 443, 1998, 93:935-960.
Drake CL, Roehrs TA, Royer H, et al., "Effects of an experimentally induced rhinovirus cold on sleep, performance, and daytime alertness." Physiol Behav 2000, 71:75-81.
Dressman HK, Muramoto GG, Chao NJ, et al., "Gene expression signatures that predict radiation exposure in mice and humans" PLoS Med 2007, 4:e106.
Falsey AR, Hennessey PA, Fmmica MA, et al., "Respiratory syncytial virus infection in elderly and high-risk adults." N Engl J Med 2005, 352:1749-1759.
Fjaerli, H-O. et la., "Whole blood gene expression in infants with respiratory syncytial virus bronchiolitis," BMC Infectious Diseases (2006) 6(175):7 pages.
Garey K W, Rege M, Pai MP, et al., "Time to initiation of fluconazole therapy impacts mortality in patients with candidemia: a multi-institutional study" Clin Infect Dis 2006, 43:25-31.

(Continued)

*Primary Examiner* — Agnieszka Boesen
(74) *Attorney, Agent, or Firm* — Michael Best & Friedrich LLP

(57) ABSTRACT

Methods of identifying infectious disease infection prior to presentation of symptoms, assays for identifying genomic markers of infectious disease, and methods for diagnosing the underlying etiology of infectious disease.

12 Claims, 9 Drawing Sheets

(56) References Cited

OTHER PUBLICATIONS

Garman KS, Acharya CR, Edelman E, et al. "A genomic approach to colon cancer risk stratification yields biologic insights into therapeutic opportunities." Proc Natl Acad Sci USA 2008, 105:19432-19437.

Gums JG, Pelletier EM, Blumentals WA, "Oseltamivir and influenza-related complications, hospitalization and healthcare expenditure in healthy adults and children." Expert Opin Pharmacother 2008,9:151-161.

Gwaltney JM, Jr., Hendley O, Hayden FG, et al., "Updated recommendations for safety-testing of viral inocula used in volunteer experiments on rhinovirus colds." Prog Med Virol 1992, 39:256-263.

Hong CY, Lin RT, Tan ES, et al., "Acute respiratory symptoms in adults in general practice." Fam Pract 2004, 21:317-323.

Jackson GG, Dowling HF, Spiesman IG, et al., "Transmission of the common cold to volunteers under controlled conditions. I. The common cold as a clinical entity." AMA Arch Intern Med 1959, 101:762-769.

Japour et al. "Standardized Peripheral Blood Mononuclear Cell Culture Assay for Determination of Drug Susceptibilities of Clinical Human Immunodeficiency Virus Type 1 Isolates" Antimicrob. Agen. Chemother. May 1993, vol. 37, No. 5, p. 1095-1101.

Jenner RG, Young RA, "Insights into host responses against pathogens from transcriptional profiling." Nat Rev Microbiol 2005, 3:281-294.

Jiang D, Guo H, Xu C, et al., "Identification of three interferon-inducible cellular enzymes that inhibit the replication of hepatitis C virus." J Virol 2008, 82:1665-1678.

Johnston SL, "Natural and experimental rhinovirus infections of the lower respiratory tract." Am J Respir Crit Care Med 1995, 152:S46-S52.

Johnstone J, Majumdar SR, Fox JD, et al., "Viral Infection in Adults Hospitalized with Community Acquired Pneumonia: Prevalence, Pathogens and Presentation." Chest 2008, 1141-1148.

Jonathan, "Diagnostic utility of BINAX NOW RSV—an evaluation of the diagnostic performance of BINAX NOW RSV in comparison with cell culture and direct immunofluorescence," Ann Clin Microbial Antimicrob (2006) vol. 5, 13.

Kirchberger S, Majdic O, Stockl J, "Modulation of the immune system by human rhinoviruses." Int Arch Allergy Immunol 2007, 142:1-10.

Kobayashi SD, Braughton KR, Whitney AR, et al., "Bacterial pathogens modulate an apoptosis differentiation program in human neutrophils." Proc Natl Acad Sci US A 2003, 100:10948-10953.

Kooperberg C, Ruczinski I, LeBlanc ML, et al., "Sequence analysis using logic regression." Gen. Epidem. 2001, 21:626-631.

Lambert SB, Whiley DM, O'Neill NT, et al., "Comparing nose-throat swabs and nasopharyngeal aspirates collected from children with symptoms for respiratory virus identification using real-time polymerase chain reaction." Pediatrics 2008, 122:e615-620.

Landry ML, Cohen S, Ferguson D: "Real-time PCR compared to Binax NOW and cytospin-immunofluorescence for detection of influenza in hospitalized patients." J Clin Virol 2008, 43:148-151.

Lee et al. "Systems-Level Comparison of Host-Responses Elicited by Avian H5N1 and Seasonal H1N1 Influenza Viruses in Primary Human Macrophages" PLoS ONE, 2009, 4(12): e8072.

Lucas JE, Carvalho CM, Merl D, et al., "In-Vitro to In-Vivo factor profiling in expression genomics." Bayesian Modeling in Bioinformatics. Edited by Dey D, Ghosh S, Mallick B: Taylor-Francis; 2008, 11-35.

Lucas JE, Carvalho CM, Wang Q, et al., Sparse statistical modelling in gene expression genomics. In Bayesian Inference for Gene Expression and Proteomics. Edited by: Cambridge University Press; 2006:155-176.

Mashimo T, Simon-Chazottes D, Guenet JL, "Innate resistance to flavivirus infections and the functions of 2'-5' oligoadenylate synthetases." Curr Top Microbial Immunol 2008, 321:85-100.

Meadows SK, Dressman HK, Muramoto GG, et al., "Gene expression signatures of radiation response are specific, durable and accurate in mice and humans." PLoS ONE 2008, 3:e1912.

Memoli MJ, Morens DM, Taubenberger JK, "Pandemic and seasonal influenza: therapeutic challenges." Drug Discov Today 2008, 13:590-595.

Min JY, Krug RM, "The primary function of RNA binding by the influenza A virus NS1 protein in infected cells: Inhibiting the 2'-5' oligo (A) synthetase/RNase L pathway." Proc Natl Acad Sci US A 2006, 103:7100-7105.

Netea MG, Brown GD, Kullberg BJ, et al.: "An integrated model of the recognition of *C albicans* by the innate immune system" Nat Rev Microbial 2008, 6:67-78.

Ostrosky-Zeichner L, Alexander BD, Kelt DH et al., "Multicenter clinical evaluation of the (1—>3) beta-D-glucan assay as an aid to diagnosis of fungal infections in humans" Clin Infect Dis 2005, 41:654-659.

Peltola V, Waris M, Osterback R, et al., "Rhinovirus transmission within families with children: incidence of symptomatic and asymptomatic infections." J Infect Dis 2008, 197:382-389.

Proud D, et al., "Gene Expression Profiles During In Vivo Human Rhinovirus Infection: Insights into the Host Response." Am J Respir Crit Care Med, Jul. 31, 2008, (pp. 1-42).

Rahman M, Vandermause MF, Kieke BA, et al., "Performance of Bin ax NOW Flu A and B and direct fluorescent assay in comparison with a composite of viral culture or reverse transcription polymerase chain reaction for detection of influenza infection during the 2006 to 2007 season." Diagn Microbial Infect Dis 2008, 62:162-166.

Rakes GP, Arruda E, Ingram JM, et al., "Rhinovirus and respiratory syncytial virus in wheezing children requiring emergency care. lgE and eosinophil analyses." Am J Respir Crit Care Med 1999, 159:785-790.

Ramilo et al., "Gene expression patterns in blood leukocytes discriminate patients with acute infections," Blood (2007) vol. 109, 2066-2077.

Rios JJ, Perelygin AA, Long MT, et al., "Characterization of the equine 2'-5' oligoadenylate synthetase 1 (OAS1) and ribonuclease L (RNASEL) innate immunity genes." BMC Genomics 2007, 8:313.

Robinson JL, Lee BE, Kothapalli S, et al., "Use of throat swab or saliva specimens for detection of respiratory viruses in children." Clin Infect Dis 2008, 46:e61-64.

Ruczinski I, Kooperberg C, LeBlanc ML, "Logic regression." J. Comp. Graph. Statist. 2003, 475-511.

Schaller M, Hogaboam CM, Lukacs N, et al., "Respiratory viral infections drive chemokine expression and exacerbate the asthmatic response." J Allergy Clin Immunol 2006, 118:295-302.

Seo D, Ginsburg GS, Goldschmidt-Clermont PJ, "Gene expression analysis of cardiovascular diseases: novel insights into biology and clinical applications." J Am Call Cardiol 2006, 48:227-235.

Seo D, Goldschmidt P, West M: "Of Mice and Men: Sparse Statistical Modeling in Cardiovascular Genomics" Annals of Applied Statistic 2007, 1: 152-178.

Simmons CP, Popper S, Dolocek C, et al., "Patterns of host genome-wide gene transcript abundance in the peripheral blood of patients with acute dengue hemorrhagic fever." J Infect Dis 2007, 195:1097-1107.

Subauste et al., "Infection of a Human Respiratory Epithelial Cell Line with Rhinovirus—Induction of Cytokine Release and Modulation of Susceptibility to Infection by Cytokine Exposure." J. Clin. Invest. 1995. 96:549-557.

Turner RB, "Ineffectiveness of intranasal zinc gluconate for prevention of experimental rhinovirus colds." Clin Infect Dis 2001, 33:1865-1870.

Wang F, Gao X, Barrett JW, et al., "RIG-I mediates the co-induction of tumor necrosis factor and type I interferon elicited by myxoma virus in primary human macrophages." PLoS Pathog 2008, 4:e1000099.

Wang Q, Carvalho CM, Lucas JE, et al., "BFRM: Bayesian factor regression modeling." Bulletin of the International Society of Bayesian Analysis 2007, 14:4-5.

Wang X, Hinson ER, Cresswell P, "The interferon-inducible protein viperin inhibits influenza virus release by perturbing lipid rafts." Cell Host Microbe 2007, 2:96-105.

Wang Z, Neuburg D, Li C, et al., "Global gene expression profiling in whole-blood samples from individuals exposed to metal fumes." Environ Health Perspect 2005, 113:233-241.

(56) References Cited

OTHER PUBLICATIONS

Xu M, Kao MC, Nunez-Iglesias J, et al., "An integrative approach to characterize disease-specific pathways and their coordination: a case study in cancer." BMC Genomics 2008, 9 Suppl 1:S12.

Zass et al., "Gene Expression Signatures Diagnose Influenza and Other Symptomatic Respiratory Viral Infections in Humans" Cell Host & Microbe Sep. 17, 2009, 6, 207-217.

Zhang, H. et al., "Signature patters revealed by microarray analyses of mice infected with influenza virus A and *Streptococcus pneumoniae*," Microbes and Infection (2006) 8:2172-2185.

Invitation to Pay Additional Fees for Application No. PCT/US2010/36257 dated Dec. 13, 2010 (3 pages).

International Search Report and Written Opinion for Application No. PCT/US2010/36257 dated Apr. 12, 2011 (16 pages).

\* cited by examiner

*RSAD2, LAMP3, IFI44L, IFIT1, SIGLEC1, IFI44, MX1, IFIT3, OAS3, SERPING1, ISG15, IFI6, OASL, LOC26010, OAS1

METHODS OF IDENTIFYING INFECTIOUS DISEASE AND ASSAYS FOR IDENTIFYING INFECTIOUS DISEASE

CROSS-REFERENCE TO RELATED APPLICATIONS

This application claims priority to and is a national stage filing under 35 U.S.C. 371 of International Application No. PCT/US2010/036257 filed on May 26, 2010, which claims the benefit of priority to U.S. Provisional Patent Application Ser. No. 61/181,216 filed on May 26, 2009, each of which is incorporated herein by reference in its entirety.

STATEMENT REGARDING FEDERALLY FUNDED RESEARCH

This invention was made with U.S. government support under grant number DARPA-N66001-09-C-2082 awarded by the Department of Defense. The government has certain rights in the invention.

FIELD OF THE INVENTION

Methods of identifying infectious disease infection prior to presentation of symptoms, assays for identifying genomic markers of infectious disease, and methods for diagnosing the underlying etiology of infectious disease. The infectious disease may result from bacterial infection, viral infection, or fungal infection. Methods for identifying the nature of an infectious disease, especially acute respiratory infections (ARI) respiratory at the point-of-care.

BACKGROUND

Acute respiratory infections (ARI) are among the most common reasons for seeking medical attention in the United States. Rhinovirus, influenza, and increasingly respiratory syncytial virus (RSV) are recognized as leading etiologies of ARI in adults. Upper respiratory tract infections caused by most viruses are generally self-limited, although among individuals with pre-existing pulmonary disease, viral infection can lead to disease exacerbation. Most adults experience at least one rhinoviral infection per year. While most rhinoviral infections are self-limited, these infections are also important causes of exacerbations of chronic obstructive pulmonary disease and asthma. Adult RSV infections may be self-limited or lead to significant airways obstruction and morbidity. Influenza infection remains common among community-living persons, with associated significant health-care and societal costs. Furthermore, new strains of influenza, such as H1N1, pose the risk of pandemic infection. Thus, early detection of influenza A can facilitate individual treatment decisions, as well as provide early data to forecast an epidemic/pandemic.

Discrimination between infectious causes of illness is a critical component of acute care of the medical patient as such distinctions facilitate both triage and treatment decisions. While traditional culture, antigen-based, and PCR based diagnostics are useful in classifying infectious pathogens, these assays are not without limitations. See, e.g., Bryant et al., "Chips with everything: DNA microarrays in infectious diseases," *Lancet Infect Dis* (2004) vol. 4, 100-111; Campbell and Ghazal, "Molecular signatures for diagnosis of infection: application of microarray technology," *J Appl Microbiol* (2004) vol. 96, 18-23, both of which are incorporated by reference in their entireties. As reported, current rapid diagnostic methods lack sensitivity. See, e.g., Jonathan, "Diagnostic utility of BINAX NOW RSV—an evaluation of the diagnostic performance of BINAX NOW RSV in comparison with cell culture and direct immunofluorescence," *Ann Clin Microbiol Antimicrob* (2006) vol. 5, 13, evaluating influenza and RSV tests of Inverness Medical Innovations (Waltham, Mass.), incorporated herein by reference in its entirety. Jonathon reports sensitivities of only 53-80%. Other know tests, such as direct-fluorescent antibody (DFA) testing, are labor-intensive and slow.

SUMMARY

In one aspect, provided are methods of identifying a subject infected with a respiratory virus comprising determining gene expression levels of at least three genes from a peripheral blood cell sample of the subject, wherein the genes are selected from the group consisting of ATF3, CCL2, CXCL10, DDX58, ETV7, FCGR1A, FCGR1B, GBP1, HERC5, IFI27, IFI44, IFI44L, IFI6, IFIT1, IFIT2, IFIT3, IFIT5, INDO, ISG15, LAMP3, LAP3, LOC26010, LOC727996, LY6E, MS4A4A, MX1, OAS1, OAS2, OAS3, OASL, PML, RSAD2, RTP4, SEPT4, SERPING1, SIGLEC1, SOCS1, TNFAIP6, and XAF1; and comparing the gene expression levels of the genes to standard gene expression levels for the genes, wherein a difference between the levels of expression of the genes and the standard gene expression levels is indicative of a subject infected with a respiratory virus.

In another aspect, provided are methods of identifying a subject infected with a respiratory virus comprising determining gene expression levels of at least three genes from a peripheral blood cell sample of the subject, wherein the genes are selected from the group consisting of ATF3, CCL2, CXCL10, DDX58, ETV7, FCGR1A, FCGR1B, GBP1, HERC5, IFI27, IFI44, IFI44L, IFI6, IFIT1, IFIT2, IFIT3, IFIT5, INDO, ISG15, LAMP3, LAP3, LOC26010, LOC727996, LY6E, MS4A4A, MX1, OAS1, OAS2, OAS3, OASL, PML, RSAD2, RTP4, SEPT4, SERPING1, SIGLEC1, SOCS1, TNFAIP6, and XAF1; and communicating the gene expression levels to a medical practitioner for the purpose of identifying a subject infected with a respiratory virus.

In another aspect, provided are methods of reducing the spread of a respiratory virus in a population comprising obtaining a peripheral blood cell sample from a subject from the population; determining gene expression levels of at least three genes from the peripheral blood cell sample of the subject, wherein the genes are selected from the group consisting of ATF3, CCL2, CXCL10, DDX58, ETV7, FCGR1A, FCGR1B, GBP1, HERC5, IFI27, IFI44, IFI44L, IFI6, IFIT1, IFIT2, IFIT3, IFIT5, INDO, ISG15, LAMP3, LAP3, LOC26010, LOC727996, LY6E, MS4A4A, MX1, OAS1, OAS2, OAS3, OASL, PML, RSAD2, RTP4, SEPT4, SERPING1, SIGLEC1, SOCS1, TNFAIP6, and XAF1; comparing the gene expression levels of the genes to standard gene expression levels for the genes, wherein a difference between the levels of expression of the genes and the standard gene expression levels is indicative of a subject infected with a respiratory virus; and isolating the subject from the population.

In another aspect, provided are methods of treating a subject suspected of having respiratory viral infection, comprising obtaining a peripheral blood cell sample from the subject; determining gene expression levels of at least three genes from the peripheral blood cell sample of the subject, wherein the genes are selected from the group consisting of ATF3, CCL2, CXCL10, DDX58, ETV7, FCGR1A, FCGR1B, GBP1, HERC5, IFI27, IFI44, IFI44L, IFI6, IFIT1, IFIT2, IFIT3, IFIT5, INDO, ISG15, LAMP3, LAP3, LOC26010, LOC727996, LY6E, MS4A4A, MX1, OAS1, OAS2, OAS3, OASL, PML, RSAD2, RTP4, SEPT4, SERPING1, SIGLEC1, SOCS1, TNFAIP6, and XAF1; comparing the gene expression levels of the genes to standard gene expression levels for the genes, wherein a difference between the levels of expression of the genes and the standard gene expression levels is indicative of a subject having a respiratory virus; and administering an anti-viral therapeutic agent.

In another aspect, provided are methods of determining gene expression levels of at least three genes selected from the group consisting of ATF3, CCL2, CXCL10, DDX58, ETV7, FCGR1A, FCGR1B, GBP1, HERC5, IFI27, IFI44, IFI44L, IFI6, IFIT1, IFIT2, IFIT3, IFIT5, INDO, ISG15, LAMP3, LAP3, LOC26010, LOC727996, LY6E, MS4A4A, MX1, OAS1, OAS2, OAS3, OASL, PML, RSAD2, RTP4, SEPT4, SERPING1, SIGLEC1, SOCS1, TNFAIP6, and XAF1 from a genetic sample, comprising assaying the genetic sample with an array comprising a plurality of nucleic acid oligomers.

In another aspect, provided is a computer readable medium comprising standard gene expression levels of least three genes selected from the group consisting of ATF3, CCL2, CXCL10, DDX58, ETV7, FCGR1A, FCGR1B, GBP1, HERC5, IFI27, IFI44, IFI44L, IFI6, IFIT1, IFIT2, IFIT3, IFIT5, INDO, ISG15, LAMP3, LAP3, LOC26010, LOC727996, LY6E, MS4A4A, MX1, OAS1, OAS2, OAS3, OASL, PML, RSAD2, RTP4, SEPT4, SERPING1, SIGLEC1, SOCS1, TNFAIP6, and XAF1 and responsivity information indicating changes in the gene expression levels of the at least three genes when a subject is infected with a respiratory virus.

In another aspect, provided are methods of identifying a type of viral respiratory infection, the methods comprising determining gene expression levels of at least ten genes from a peripheral blood cell sample of the subject, wherein the genes are selected from the group consisting of ATF3, CCL2, CXCL10, DDX58, ETV7, FCGR1A, FCGR1B, GBP1, HERC5, IFI27, IFI44, IFI44L, IFI6, IFIT1, IFIT2, IFIT3, IFIT5, INDO, ISG15, LAMP3, LAP3, LOC26010, LOC727996, LY6E, MS4A4A, MX1, OAS1, OAS2, OAS3, OASL, PML, RSAD2, RTP4, SEPT4, SERPING1, SIGLEC1, SOCS1, TNFAIP6, and XAF1; comparing the gene expression levels of at least three of the genes to standard gene expression levels for a rhinovirus gene set comprising RSAD2, LAMP3, IFI44L, IFIT1, SIGLEC1, IFI44, OAS3, LOC727996, SERPING1, HERC5, ISG15, IFI6, IFI44, INDO, MX1, IFIT3, OASL, LOC26010, OASL, CXCL10, ATF3, OAS1, DDX58, OAS1, LY6E, OAS2, CCL2, XAF1, IFIT2, and SOCS1, wherein a difference between the levels of expression of the genes and the standard gene expression levels for a rhinovirus gene set is indicative of a subject infected with rhinovirus; comparing the gene expression levels of at least three of the genes to standard gene expression levels for a respiratory syncytial virus gene set comprising RSAD2, SERPING1, IFI44L, IFIT1, IFI44, LAMP3, OAS3, HERC5, ISG15, IFIT3, SIGLEC1, OASL, OAS1, LOC26010, MX1, IFI6, FCGR1A, GBP1, ATF3, IFIT5, LAP3, OASL, IFIT2, RTP4, GBP1, DDX58, ETV7, FCGR1B, and OAS1, wherein a difference between the levels of expression of the genes and the standard gene expression levels for a respiratory syncytial virus gene set is indicative of a subject infected with respiratory syncytial virus; and comparing the gene expression levels of at least three of the genes to standard gene expression levels for an influenza gene set comprising RSAD2, IFI44L, SIGLEC1, LAMP3, IFIT1, IFI44, SERPING1, IFI27, ISG15, HERC5, LOC26010, IFI6, LOC727996, IFIT3, OAS3, OASL, SEPT4, XAF1, OAS1, LY6E, MS4A4A, SIGLEC1, TNFAIP6, CCL2, OAS1, MX1, TNFAIP6, RTP4, and OASL, and SOCS1, wherein a difference between the levels of expression of the genes and the standard gene expression levels for an influenza gene set is indicative of a subject infected with influenza.

In another aspect, provided are methods of screening a compound for efficacy against rhinovirus, comprising determining first gene expression levels of at least three genes from a cell culture wherein the genes are selected from the group consisting of ATF3, CCL2, CXCL10, DDX58, ETV7, FCGR1A, FCGR1B, GBP1, HERC5, IFI27, IFI44, IFI44L, IFI6, IFIT1, IFIT2, IFIT3, IFIT5, INDO, ISG15, LAMP3, LAP3, LOC26010, LOC727996, LY6E, MS4A4A, MX1, OAS1, OAS2, OAS3, OASL, PML, RSAD2, RTP4, SEPT4, SERPING1, SIGLEC1, SOCS1, TNFAIP6, and XAF1; inoculating the cell culture with rhinovirus; determining second gene expression levels of the genes from the cell culture at a time later than step b) to determine the infection status of the cell culture, wherein an increase between the first and second gene expression levels is indicative of a cell culture infected with rhinovirus; contacting the infected cell culture with a compound; and determining third gene expression levels of the genes from the cell culture at a time later than step d) to determine the infection status of the cell culture, wherein a decrease between the second and third gene expression levels is indicative of a compound having efficacy against rhinovirus.

In another aspect, provided are methods of screening a compound for efficacy against respiratory syncytial virus, comprising determining first gene expression levels of at least three genes from a cell culture, wherein the genes are selected from the group consisting of RSAD2, SERPING1, IFI44L, IFIT1, IFI44, LAMP3, OAS3, HERC5, ISG15, IFIT3, SIGLEC1, OASL, OAS1, LOC26010, MX1, IFI6, FCGR1A, GBP1, ATF3, IFIT5, LAP3, OASL, IFIT2, RTP4, GBP1, DDX58, ETV7, FCGR1B, and OAS1; inoculating the cell culture with respiratory syncytial virus; determining second gene expression levels of the genes from the cell culture at a time later than step b) to determine the infection status of the cell culture, wherein an increase between the first and second gene expression levels is indicative of a cell culture infected with respiratory syncytial virus; contacting the infected cell culture with a compound; and determining third gene expression levels of the genes from the cell culture at a time later than step d) to determine the infection status of the cell culture, wherein a decrease between the second and third gene expression levels is indicative of a compound having efficacy against respiratory syncytial virus.

In another aspect, provided are methods of screening a compound for efficacy against influenza, comprising determining first gene expression levels of at least three genes from a cell culture, wherein the genes are selected from the group consisting of RSAD2, SERPING1, IFI44L, IFIT1, IFI44, LAMP3, OAS3, HERC5, ISG15, IFIT3, SIGLEC1, OASL, OAS1, LOC26010, MX1, IFI6, FCGR1A, GBP1, ATF3, IFIT5, LAP3, OASL, IFIT2, RTP4, GBP1, DDX58, ETV7, FCGR1B, and OAS1; inoculating the cell culture with influenza; determining second gene expression levels of the genes from the cell culture at a time later than step b) to determine the infection status of the cell culture, wherein an increase between the first and second gene expression levels is indicative of a cell culture infected with influenza; contacting the infected cell culture with a compound; and determining third gene expression levels of the genes from the cell culture at a time later than step d) to determine the infection status of the cell culture, wherein a decrease between the second and third gene expression levels is indicative of a compound having efficacy against influenza.

In another aspect, provided are methods of screening a compound for therapeutic efficacy against rhinovirus, comprising determining first gene expression levels of at least three genes from a first peripheral blood cell sample of a test subject, wherein the genes are selected from the group consisting of ATF3, CCL2, CXCL10, DDX58, ETV7, FCGR1A, FCGR1B, GBP1, HERC5, IFI27, IFI44, IFI44L, IFI6, IFIT1, IFIT2, IFIT3, IFIT5, INDO, ISG15, LAMP3, LAP3, LOC26010, LOC727996, LY6E, MS4A4A, MX1, OAS1, OAS2, OAS3, OASL, PML, RSAD2, RTP4, SEPT4, SERPING1, SIGLEC1, SOCS1, TNFAIP6, and XAF1; inoculating the test subject with rhinovirus; determining second gene expression levels of the genes from a second peripheral blood cell sample of the test subject at a time later than step b) to determine the infection status of the test subject, wherein an increase between the first and second gene expression levels is indicative of a test subject infected with rhinovirus; administering the compound to the test subject infected with rhinovirus; and determining third gene expression levels of the genes from a third peripheral blood cell sample of the test subject at a time later than step d) to determine the infection status of the test subject, wherein a decrease between the second and third gene expression levels is indicative of a compound having therapeutic efficacy against rhinovirus.

In another aspect, provided are methods of screening a compound for therapeutic efficacy against respiratory syncytial virus, comprising determining first gene expression levels of at least three genes from a first peripheral blood cell sample of a test subject, wherein the genes are selected from the group consisting of RSAD2, SERPING1, IFI44L, IFIT1, IFI44, LAMP3, OAS3, HERC5, ISG15, IFIT3, SIGLEC1, OASL, OAS1, LOC26010, MX1, IFI6, FCGR1A, GBP1, ATF3, IFIT5, LAP3, OASL, IFIT2, RTP4, GBP1, DDX58, ETV7, FCGR1B, and OAS1; inoculating the test subject with respiratory syncytial virus; determining second gene expression levels of the genes from a second peripheral blood cell sample of the test subject at a time later than step b) to determine the infection status of the test subject, wherein an increase between the first and second gene expression levels is indicative of a test subject infected with respiratory syncytial virus; administering the compound to the test subject infected with respiratory syncytial virus; and determining third gene expression levels of the genes from a third peripheral blood cell sample of the test subject at a time later than step d) to determine the infection status of the test subject, wherein a decrease between the second and third gene expression levels is indicative of a compound having therapeutic efficacy against respiratory syncytial virus.

In another aspect, provided are methods of screening a compound for therapeutic efficacy against influenza, comprising determining first gene expression levels of at least three genes from a first peripheral blood cell sample of a test subject, wherein the genes are selected from the group consisting of RSAD2, SERPING1, IFI44L, IFIT1, IFI44, LAMP3, OAS3, HERC5, ISG15, IFIT3, SIGLEC1, OASL, OAS1, LOC26010, MX1, IFI6, FCGR1A, GBP1, ATF3, IFIT5, LAP3, OASL, IFIT2, RTP4, GBP1, DDX58, ETV7, FCGR1B, and OAS1; inoculating the test subject with influenza; determining second gene expression levels of the genes from a second peripheral blood cell sample of the test subject at a time later than step b) to determine the infection status of the test subject, wherein an increase between the first and second gene expression levels is indicative of a test subject infected with influenza; administering the compound to the test subject infected with influenza; and determining third gene expression levels of the genes from a third peripheral blood cell sample of the test subject at a time later than step d) to determine the infection status of the test subject, wherein a decrease between the second and third gene expression levels is indicative of a compound having therapeutic efficacy against influenza.

In another aspect, provided are methods of determining the pharmacokinetic activity of a compound against rhinovirus, comprising determining first gene expression levels of at least three genes from a first peripheral blood cell sample of a test subject, wherein the genes are selected from the group consisting of ATF3, CCL2, CXCL10, DDX58, ETV7, FCGR1A, FCGR1B, GBP1, HERC5, IFI27, IFI44, IFI44L, IFI6, IFIT1, IFIT2, IFIT3, IFIT5, INDO, ISG15, LAMP3, LAP3, LOC26010, LOC727996, LY6E, MS4A4A, MX1, OAS1, OAS2, OAS3, OASL, PML, RSAD2, RTP4, SEPT4, SERPING1, SIGLEC1, SOCS1, TNFAIP6, and XAF1; inoculating the test subject with rhinovirus; determining second gene expression levels of the genes from a second peripheral blood cell sample of the test subject at a time later than step b) to determine the infection status of the test subject, wherein an increase between the first and second gene expression levels is indicative of a test subject infected with rhinovirus; administering the compound to the test subject infected with rhinovirus; and determining third gene expression levels of the genes from a third peripheral blood cell sample of the test subject at a time later than step d) to determine the infection status of the test subject, wherein a decrease between the second and third gene expression levels is indicative of a compound having therapeutic efficacy against rhinovirus.

In another aspect, provided are methods of determining the pharmacokinetic activity of a compound against respiratory syncytial virus, comprising determining first gene expression levels of at least three genes from a first peripheral blood cell sample of a test subject, wherein the genes are selected from the group consisting of RSAD2, SERPING1, IFI44L, IFIT1, IFI44, LAMP3, OAS3, HERC5, ISG15, IFIT3, SIGLEC1, OASL, OAS1, LOC26010, MX1, IFI6, FCGR1A, GBP1, ATF3, IFIT5, LAP3, OASL, IFIT2, RTP4, GBP1, DDX58, ETV7, FCGR1B, and OAS1; inoculating the test subject with respiratory syncytial virus; determining second gene expression levels of the genes from a second peripheral blood cell sample of the test subject at a time later than step b) to determine the infection status of the test subject, wherein an increase between the first and second gene expression levels is indicative of a test subject infected with respiratory syncytial virus; administering the compound to the test subject infected with respiratory syncytial virus; and determining third gene expression levels of the genes from a third peripheral blood cell sample of the test subject at a time later than step d) to determine the infection status of the test subject, wherein a decrease between the second and third gene expression levels is indicative of a compound having therapeutic efficacy against respiratory syncytial virus.

In another aspect, provided are methods of determining the pharmacokinetic activity of a compound against influenza, comprising determining first gene expression levels of at least three genes from a first peripheral blood cell sample of a test subject, wherein the genes are selected from the group consisting of RSAD2, SERPING1, IFI44L, IFIT1, IFI44, LAMP3, OAS3, HERC5, ISG15, IFIT3, SIGLEC1, OASL, OAS1, LOC26010, MX1, IFI6, FCGR1A, GBP1, ATF3, IFIT5, LAP3, OASL, IFIT2, RTP4, GBP1, DDX58, ETV7, FCGR1B, and OAS1; inoculating the test subject with influenza; determining second gene expression levels of the genes from a second peripheral blood cell sample of the test subject at a time later than step b) to determine the infection status of the test subject, wherein an increase between the first and second gene expression levels is indicative of a test subject infected with influenza; administering the compound to the test subject infected with influenza; and determining third gene expression levels of the genes from a third peripheral blood cell sample of the test subject at a time later than step d) to determine the infection status of the test subject, wherein a decrease between the second and third gene expression levels is indicative of a compound having therapeutic efficacy against influenza.

In another aspect, provided are methods for determining an effective dose of a compound to effectively reduce a rhinovirus infection in a subject, comprising determining first gene expression levels of at least three genes from a first peripheral blood cell sample of a test subject, wherein the genes are selected from the group consisting of ATF3, CCL2, CXCL10, DDX58, ETV7, FCGR1A, FCGR1B, GBP1, HERC5, IFI27, IFI44, IFI44L, IFI6, IFIT1, IFIT2, IFIT3, IFIT5, INDO, ISG15, LAMP3, LAP3, LOC26010, LOC727996, LY6E, MS4A4A, MX1, OAS1, OAS2, OAS3, OASL, PML, RSAD2, RTP4, SEPT4, SERPING1, SIGLEC1, SOCS1, TNFAIP6, and XAF1; inoculating the test subject with rhinovirus; determining second gene expression levels of the genes from a second peripheral blood cell sample of the test subject at a time later than step b) to determine the infection status of the test subject, wherein an increase between the first and second gene expression levels is indicative of a test subject infected with rhinovirus; administering a dose of the compound to the test subject infected with rhinovirus; determining third gene expression levels of the genes from a third peripheral blood cell sample of the test subject at a time later than step d); and comparing the third gene expression levels to the first gene expression levels to determine if the dose effectively reduced the rhinovirus infection in the subject.

In another aspect, provided are methods for determining an effective dose of a compound to reduce a respiratory syncytial infection in a subject, comprising determining first gene expression levels of at least three genes from a first peripheral blood cell sample of a test subject, wherein the genes are selected from the group consisting of RSAD2, SERPING1, IFI44L, IFIT1, IFI44, LAMP3, OAS3, HERC5, ISG15, IFIT3, SIGLEC1, OASL, OAS1, LOC26010, MX1, IFI6, FCGR1A, GBP1, ATF3, IFIT5, LAP3, OASL, IFIT2, RTP4, GBP1, DDX58, ETV7, FCGR1B, and OAS1; inoculating the test subject with respiratory syncytial virus; determining second gene expression levels of the genes from a second peripheral blood cell sample of the test subject at a time later than step b) to determine the infection status of the test subject, wherein an increase between the first and second gene expression levels is indicative of a test subject infected with respiratory syncytial virus; administering a dose of the compound to the test subject infected with respiratory syncytial virus; determining third gene expression levels of the genes from a third peripheral blood cell sample of the test subject at a time later than step d); and comparing the third gene expression levels to the first gene expression levels to determine if the dose effectively reduced the respiratory syncytial virus infection in the subject.

In another aspect, provided are methods for determining an effective dose of a compound to reduce an influenza infection in a subject, comprising determining first gene expression levels of at least three genes from a first peripheral blood cell sample of a test subject, wherein the genes are selected from the group consisting of RSAD2, SERPING1, IFI44L, IFIT1, IFI44, LAMP3, OAS3, HERC5, ISG15, IFIT3, SIGLEC1, OASL, OAS1, LOC26010, MX1, IFI6, FCGR1A, GBP1, ATF3, IFIT5, LAP3, OASL, IFIT2, RTP4, GBP1, DDX58, ETV7, FCGR1B, and OAS1; inoculating the test subject with influenza; determining second gene expression levels of the genes from a second peripheral blood cell sample of the test subject at a time later than step b) to determine the infection status of the test subject, wherein an increase between the first and second gene expression levels is indicative of a test subject infected with influenza; administering a dose of the compound to the test subject infected with influenza; determining third gene expression levels of the genes from a third peripheral blood cell sample of the test subject at a time later than step d); and comparing the third gene expression levels to the first gene expression levels to determine if the dose effectively reduced the influenza infection in the subject.

In another aspect, provided are methods of identifying a subject infected with a respiratory virus comprising determining protein expression levels of at least three proteins from a peripheral blood cell sample of the subject, wherein the proteins are selected from the group consisting of AFAM, ACTG, LUM, AACT, SAMP, FHR1, APOH, HRG, APOA4, A2GL, CFAB, CO7, APOB, KAIN, CHLE, APOE, ITIH4, Myeloperoxidase, MMP-2, Myoglobin, and IgE; and comparing the protein expression levels of the proteins to standard protein expression levels for the proteins, wherein a difference between the levels of expression of the proteins and the standard protein expression levels is indicative of a subject infected with a respiratory virus.

In another aspect, provided are methods of identifying a subject infected with a respiratory virus comprising determining protein expression levels of at least three proteins from a peripheral blood cell sample of the subject, wherein the proteins are selected from the group consisting of AFAM, ACTG, LUM, AACT, SAMP, FHR1, APOH, HRG, APOA4, A2GL, CFAB, CO7, APOB, KAIN, CHLE, APOE, ITIH4, Myeloperoxidase, MMP-2, Myoglobin, and IgE; and communicating the protein expression levels to a medical practitioner for the purpose of identifying a subject infected with a respiratory virus.

In another aspect, provided are methods of reducing the spread of a respiratory virus in a population comprising obtaining a peripheral blood cell sample from a subject from the population; determining protein expression levels of at least three proteins from the peripheral blood cell sample of the subject, wherein the proteins are selected from the group consisting of AFAM, ACTG, LUM, AACT, SAMP, FHR1, APOH, HRG, APOA4, A2GL, CFAB, CO7, APOB, KAIN, CHLE, APOE, ITIH4, Myeloperoxidase, MMP-2, Myoglobin, and IgE; comparing the protein expression levels of the proteins to standard protein expression levels for the proteins, wherein a difference between the levels of expression of the proteins and the standard protein expression levels is indicative of a subject infected with a respiratory virus; and isolating the subject from the population.

In another aspect, provided are methods of treating a subject suspected of having respiratory viral infection, comprising obtaining a peripheral blood cell sample from the subject; determining protein expression levels of at least three proteins from the peripheral blood cell sample of the subject, wherein the proteins are selected from the group consisting of AFAM, ACTG, LUM, AACT, SAMP, FHR1, APOH, HRG, APOA4, A2GL, CFAB, CO7, APOB, KAIN, CHLE, APOE, ITIH4, Myeloperoxidase, MMP-2, Myoglobin, and IgE; comparing the protein expression levels of the proteins to standard protein expression levels for the proteins, wherein a difference between the levels of expression of the proteins and the standard protein expression levels is indicative of a subject having a respiratory virus; and administering an anti-viral therapeutic agent.

In another aspect, provided are methods of determining protein expression levels of at least three proteins selected from the group consisting of AFAM, ACTG, LUM, AACT, SAMP, FHR1, APOH, HRG, APOA4, A2GL, CFAB, CO7, APOB, KAIN, CHLE, APOE, ITIH4, Myeloperoxidase, MMP-2, Myoglobin, and IgE from a sample, comprising assaying the sample with an array comprising a plurality of antibodies.

In another aspect, provided are methods of identifying a subject infected with a respiratory virus comprising determining metabolite levels of at least three metabolites from a peripheral blood cell sample of the subject, wherein the metabolites are selected from the group consisting of His, Glx, C8:1, Adiponectin, C4/Ci4, C5:1, C20; and comparing the metabolite levels of the metabolites to standard metabolite levels for the metabolites, wherein a difference between the levels of expression of the metabolites and the standard metabolite levels is indicative of a subject infected with a respiratory virus.

In another aspect, provided are methods of identifying a subject infected with a respiratory virus comprising determining metabolite levels of at least three metabolites from a peripheral blood cell sample of the subject, wherein the metabolites are selected from the group consisting of His, Glx, C8:1, Adiponectin, C4/Ci4, C5:1, C20; and communicating the metabolite levels to a medical practitioner for the purpose of identifying a subject infected with a respiratory virus.

In another aspect, provided are methods of reducing the spread of a respiratory virus in a population comprising obtaining a peripheral blood cell sample from a subject from the population; determining metabolite levels of at least three metabolites from the peripheral blood cell sample of the subject, wherein the metabolites are selected from the group consisting of His, Glx, C8:1, Adiponectin, C4/Ci4, C5:1, C20; comparing the metabolite levels of the metabolites to standard metabolite levels for the metabolites, wherein a difference between the levels of expression of the metabolites and the standard metabolite levels is indicative of a subject infected with a respiratory virus; and isolating the subject from the population.

In another aspect, provided are methods of treating a subject suspected of having respiratory viral infection, comprising obtaining a peripheral blood cell sample from the subject; determining metabolite levels of at least three metabolites from the peripheral blood cell sample of the subject, wherein the metabolites are selected from the group consisting of His, Glx, C8:1, Adiponectin, C4/Ci4, C5:1, C20; comparing the metabolite levels of the metabolites to standard metabolite levels for the metabolites, wherein a difference between the levels of expression of the metabolites and the standard metabolite levels is indicative of a subject having a respiratory virus; and administering an anti-viral therapeutic agent.

In another aspect, provided are methods of determining metabolite levels of at least three metabolites selected from the group consisting of His, Glx, C8:1, Adiponectin, C4/Ci4, C5:1, C20 from a sample, comprising assaying the sample with an array comprising a plurality of antibodies.

In another aspect, provided are methods of distinguishing between a viral respiratory infection and a bacterial respiratory infection in a subject comprising determining gene expression levels of at least three genes from a peripheral blood cell sample of the subject, wherein the genes are selected from the group consisting of ATF3, CCL2, CXCL10, DDX58, ETV7, FCGR1A, FCGR1B, GBP1, HERC5, IFI27, IFI44, IFI44L, IFI6, IFIT1, IFIT2, IFIT3, IFIT5, INDO, ISG15, LAMP3, LAP3, LOC26010, LOC727996, LY6E, MS4A4A, MX1, OAS1, OAS2, OAS3, OASL, PML, RSAD2, RTP4, SEPT4, SERPING1, SIGLEC1, SOCS1, TNFAIP6, and XAF1; and comparing the gene expression levels of the genes to standard gene expression levels for the genes, wherein a difference between the levels of expression of the genes and the standard gene expression levels is indicative of a subject infected with a respiratory virus.

In another aspect, provided are methods of distinguishing between a viral respiratory infection and a bacterial respiratory infection in a subject comprising determining gene expression levels of at least three genes from a peripheral blood cell sample of the subject, wherein the genes are selected from the group consisting of ATF3, CCL2, CXCL10, DDX58, ETV7, FCGR1A, FCGR1B, GBP1, HERC5, IFI27, IFI44, IFI44L, IFI6, IFIT1, IFIT2, IFIT3, IFIT5, INDO, ISG15, LAMP3, LAP3, LOC26010, LOC727996, LY6E, MS4A4A, MX1, OAS1, OAS2, OAS3, OASL, PML, RSAD2, RTP4, SEPT4, SERPING1, SIGLEC1, SOCS1, TNFAIP6, and XAF1; and communicating the gene expression levels to a medical practitioner for the purpose of distinguishing between a viral respiratory infection and a bacterial respiratory infection.

In another aspect, provided are methods of treating a subject suspected of having either a viral respiratory infection or a bacterial respiratory infection, comprising obtaining a peripheral blood cell sample from the subject; determining gene expression levels of at least three genes from the peripheral blood cell sample of the subject, wherein the genes are selected from the group consisting of ATF3, CCL2, CXCL10, DDX58, ETV7, FCGR1A, FCGR1B, GBP1, HERC5, IFI27, IFI44, IFI44L, IFI6, IFIT1, IFIT2, IFIT3, IFIT5, INDO, ISG15, LAMP3, LAP3, LOC26010, LOC727996, LY6E, MS4A4A, MX1, OAS1, OAS2, OAS3, OASL, PML, RSAD2, RTP4, SEPT4, SERPING1, SIGLEC1, SOCS1, TNFAIP6, and XAF1; comparing the gene expression levels of the genes to standard gene expression levels for the genes, wherein a difference between the levels of expression of the genes and the standard gene expression levels is indicative of a subject having a respiratory virus; and administering an effective amount of a therapeutic agent to the subject.

In another aspect, a method of selecting a treatment for a subject suspected of having either a viral respiratory infection or a bacterial respiratory infection, comprising a) obtaining a peripheral blood cell sample from the subject, b) determining gene expression levels of at least three genes from the peripheral blood cell sample of the subject, wherein the genes are selected from the group consisting of ATF3, CCL2, CXCL10, DDX58, ETV7, FCGR1A, FCGR1B, GBP1, HERC5, IFI27, IFI44, IFI44L, IFI6, IFIT1, IFIT2, IFIT3, IFIT5, INDO, ISG15, LAMP3, LAP3, LOC26010, LOC727996, LY6E, MS4A4A, MX1, OAS1, OAS2, OAS3, OASL, PML, RSAD2, RTP4, SEPT4, SERPING1, SIGLEC1, SOCS1, TNFAIP6, and XAF1, c) comparing the gene expression levels of the genes to standard gene expression levels for the genes, wherein a difference between the levels of expression of the genes and the standard gene expression levels is indicative of a subject having a respiratory virus, d) administering an anti-viral therapeutic or no therapeutic if the subject has a respiratory virus, or e) administering an antibiotic if the subject does not have a respiratory virus.

In another aspect, a method of treating a subject with a viral respiratory infection comprising a) obtaining a peripheral blood cell sample from the subject, b) determining gene expression levels of at least three genes from the peripheral blood cell sample of the subject, wherein the genes are selected from the group consisting of ATF3, CCL2, CXCL10, DDX58, ETV7, FCGR1A, FCGR1B, GBP1, HERC5, IFI27, IFI44, IFI44L, IFI6, IFIT1, IFIT2, IFIT3, IFIT5, INDO, ISG15, LAMP3, LAP3, LOC26010, LOC727996, LY6E, MS4A4A, MX1, OAS1, OAS2, OAS3, OASL, PML, RSAD2, RTP4, SEPT4, SERPING1, SIGLEC1, SOCS1, TNFAIP6, and XAF1, c) comparing the gene expression levels of the genes to standard gene expression levels for the genes for a population presenting severe symptoms of respiratory infection, wherein the subject is a member of the population, d) determining whether the subject is likely to develop severe symptoms of respiratory infection, and e) administering an anti-viral therapeutic if the subject is likely to develop severe symptoms of respiratory infection.

In another aspect, a computer readable medium comprising standard protein expression levels of least three proteins selected from the group consisting of AFAM, ACTG, LUM, AACT, SAMP, FHR1, APOH, HRG, APOA4, A2GL, CFAB, CO7, APOB, KAIN, CHLE, APOE, ITIH4, Myeloperoxidase, MMP-2, Myoglobin, and IgE, and responsivity information indicating changes in the protein expression levels of the at least three proteins when a subject is infected with a respiratory virus.

Other aspects of the invention can become apparent by consideration of the detailed description and accompanying drawings.

DETAILED DESCRIPTION

Figure 1:
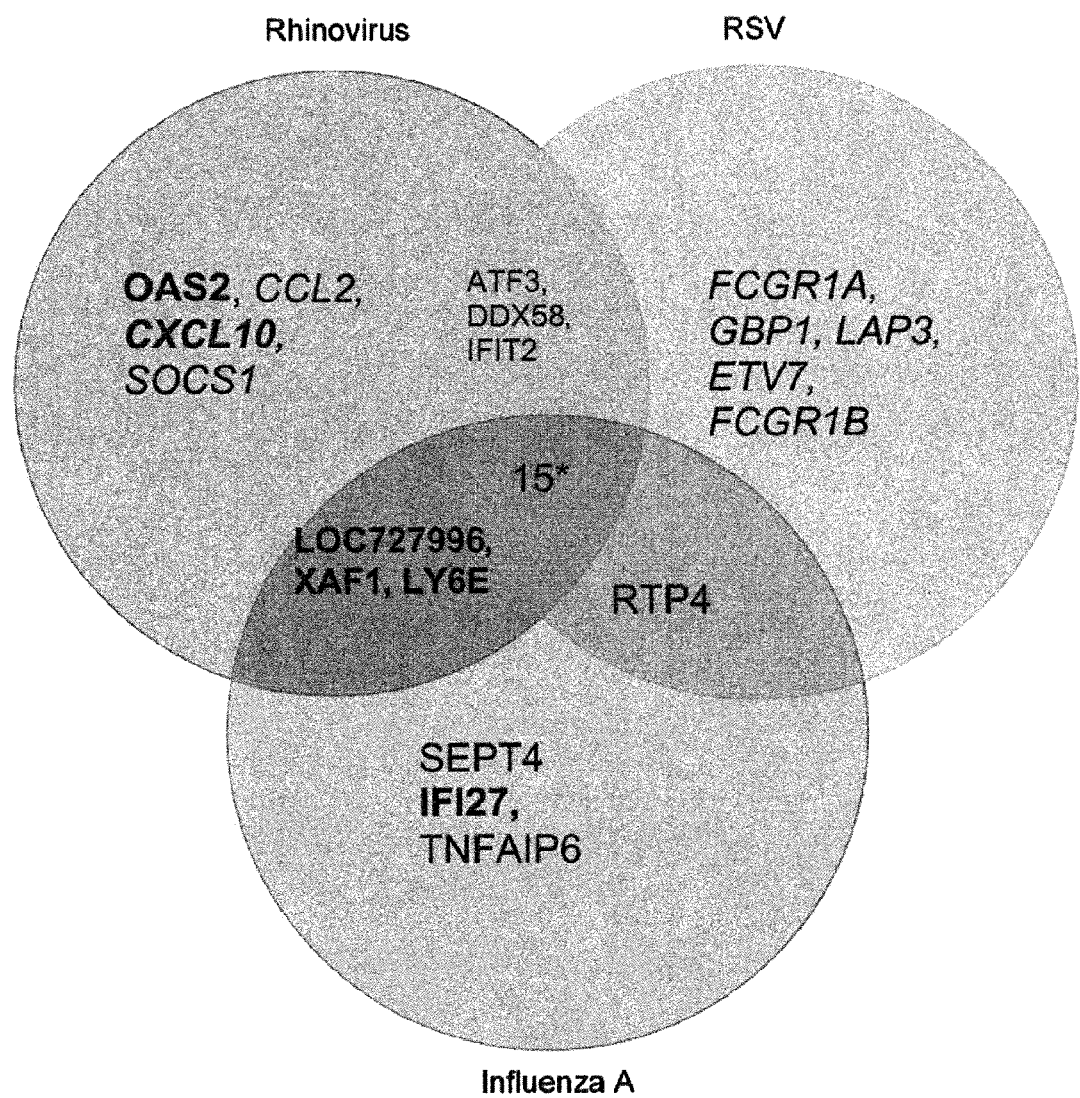
FIG. 1 is a Venn diagram showing the overlap between gene sets for rhinovirus, respiratory syncytial virus, and influenza. The "panviral" gene set corresponds to the intersection of the three circles.

Rhinovirus, RSV, and influenza are all spread by droplet inhalation, and upon contact with the respiratory epithelium, these viruses initiate a cytokine and chemokine response that orchestrates proliferation, chemotaxis and amplification of inflammatory cells. Nasal epithelial inflammation produced on contact with virus triggers a coordinated host response that may result in infection limited to the upper respiratory tract or spread to the lower respiratory tract with bronchiolitis and pneumonia. Understanding the key responses to these common infections can allow for better understanding of disease pathobiology as well provide a basis for development of novel diagnostic methodologies for distinguishing viral respiratory infection from respiratory disease caused by other common pathogens.

Early, accurate detection of infection in high risk patients has profound implications for improvement in diagnosis and initiation of appropriate therapy. Compelling evidence already exists that the host response to pathogen invasion, in the form of pathogen-specific gene expression signatures, can serve as a primary diagnostic or to corroborate current diagnostics. Importantly, both laboratory and statistical research have established that murine-derived gene expression signatures can be used to classify human disease states. Early detection typically refers to detection prior to the presentation of symptoms in a subject. For example, respiratory viral and bacterial infections may present symptoms such as runny nose, sneezing, earache, cough, shortness of breath, malaise, myalgias, headache, stuffy nose, sore throat. More severe conditions may present symptoms such as fevers, weight loss, and pain. In some instances, it is possible to distinguish between subjects that are infected with a respiratory virus that will develop symptoms and those that will not develop symptoms.

Peripheral blood leukocytes represent a reservoir and migration point for cells involved in many aspects of host immune response. Gene expression patterns obtained from peripheral blood cells can discriminate between various physiologic states as well as exposures to pathogens, immune modifiers (e.g., LPS), and environmental exposures. While current infectious disease diagnostics rely heavily on pathogen-based detection, the development of reproducible means for extracting whole blood RNA, coupled with advanced statistical methods for analysis of complex datasets, now allows the possibility of classifying infections based on host gene expression profiling that reveal pathogen specific signatures of disease.

Whole blood gene expression patterns, captured by micro arrays, for example, offer a robust means of classifying infectious pathogens, and provide a means of early and specific diagnosis well in advance of standard methods of detection of infection. Rapid and accurate pathogen classification in this setting allows for increased antimicrobial precision and provides for the identification of specific pathways involved in host response to various infectious pathogens. With continuing advances in microanalytics, it is foreseeable that the methods claimed herein will become the basis for point-of-care diagnostics that allow for rapid and inexpensive screening for viral respiratory infection. Early detection may result in significant cost saving to the medical system as infectious subjects can be quarantined from the general population and misdiagnosis of viral respiratory infection is reduced.

The invention concerns methods and assays for the early and accurate identification of persons that can develop an infectious illness. Community-acquired acute respiratory infections (CARI) represent the most likely infectious disorder that can substantially decrease individual effectiveness. The host response to respiratory pathogens begins upon exposure and may be silent for days to weeks prior to the development of clinical symptoms. The invention discloses a predictive model, diagnostic test platforms, and assays for detecting presymptomatic exposure and prediction of future illness. The methods and assays of the invention can allow for early detection of exposure to infectious pathogens, thus allowing quarantine and/or treatment of pre-symptomatic subjects. The methods may similarly be incorporated into broader epidemiological studies of populations based upon geographic location and/or genetic identity.

Through the use of independent human viral challenge studies it is possible to define host-based peripheral blood gene expression patterns characteristic of response to viral respiratory infection, i.e., rhinovirus, RSV, or influenza. The results provide clear evidence that a unique biologically-relevant peripheral blood gene expression signature predicts respiratory viral infection with a remarkable degree of accuracy. These findings underscore the conserved nature of the host response to viral infection, which is also evident in the cross-validation between experimental cohorts. The conservation of host response to viral infection is additionally evident from the overlap in viral signatures among the three viral challenge groups. This so-called "panviral" gene expression signature, derived from these cohorts, can be validated in an independently derived external dataset and used to distinguish respiratory viral infection from bacterial infection. Overall, these findings provide compelling evidence that peripheral blood gene expression can function as a biomarker for specific classes of infectious pathogens and may potentially serve as a useful diagnostic for triaging treatment decisions for upper respiratory infection.

The term "indicative" when used with gene expression levels means that the gene expression levels are up-regulated or down-regulated, altered, or changed compared to the standard gene expression levels. The term "indicative" when used with protein levels means that the protein levels are higher or lower, increased or decreased, altered, or changed compared to the standard protein levels.

The term "standard gene expression levels" refers to the gene expression levels in a subject or member of a population that does not have a viral respiratory infection, for example, a subject or member that is not infected with rhinovirus, respiratory syncytial virus, or influenza. The term "standard protein levels" refers to the protein levels in a subject or member of a population that does not have a viral respiratory infection, for example, a subject or member that is not infected with rhinovirus, respiratory syncytial virus, or influenza. The factors for determining a population include race, gender, age, geographic location and ethnic origin. In one embodiment, the standard gene expression levels for the genes are the average expression levels of the genes for a non-infected population to which the subject belongs, e.g., adult American female or male, or for a particular subject prior to being infected. A difference between the levels of expression of the genes and the standard gene expression levels is indicative of a subject having a viral respiratory infection. For example, a peripheral blood sample may be obtained from a subject at a medical laboratory, the blood sample worked up and screened for gene expression, the results of the screening compared to the gene expression standards, and the subject informed of her infectious status.

The term "bacteremia standard gene expression levels" refers to the gene expression levels in subject or member of a population that has bacteremia, for example, a subject or member of a population that is infected with Staphylococcus aureus. The standard gene expression levels for the genes are the average expression levels of the genes for a non-infected population to which the subject belongs, e.g., adult American female or male, or for a particular subject prior to being infected. In one embodiment, a difference between the levels of expression of the genes and the bacteremia standard gene expression levels is indicative of a subject having candidiasis. In another embodiment, a difference between the levels of expression of the genes and the bacteremia standard gene expression levels is indicative of a subject having bacteremia.

The term "subject" refers to any animal being examined, studied or treated. It is not intended that the present invention be limited to any particular type of subject. In some embodiments of the present invention, humans are the preferred subject, while in other embodiments nonhuman animals are the preferred subject, including but not limited to mice, monkeys, ferrets, cattle, sheep, goats, pigs, chicken, turkeys, dogs, cats, horses and reptiles.

The terms "array," "microarray" and "micro array" are interchangeable and refer to an arrangement of a collection of nucleotide sequences in a centralized location. Arrays can be on a solid substrate, such as a glass slide, or on a semi-solid substrate, such as nitrocellulose membrane. The nucleotide sequences can be DNA, RNA, or any permutations thereof. The nucleotide sequences can also be partial sequences from a gene, primers, whole gene sequences, non-coding sequences, coding sequences, published sequences, known sequences, or novel sequences. The arrays may additionally comprise antibodies, or other compounds that specifically bind proteins or metabolites.

The term "effective amount" refers to an amount of a therapeutic agent that is sufficient to exert a physiological effect in the subject.

The term "computer readable medium" refers to any device or system for storing and providing information (e.g., data and instructions) to a computer processor. Examples of computer readable media include, but are not limited to, DVDs, CDs hard disk drives, magnetic tape and servers for streaming media over networks. In various embodiments, aspects of the present invention including data structures and methods may be stored on a computer readable medium.

The term "responsivity" refers to a change in gene expression levels of genes in a subject in response to the subject being infected with candidiasis compared to the gene expression levels of the genes in a subject that is not infected with candidiasis or a control subject.

The term "peripheral blood sample" refers to a sample of cardiology blood circulating in the system or body taken from the system of body.

The term "genetic material" refers to a material used to store genetic information in the nuclei or mitochondria of an organism's cells. Examples of genetic material include, but are not limited to double-stranded and single-stranded DNA, RNA, and mRNA.

The term "plurality of nucleic acid oligomers" refers to two or more nucleic acid oligomers, which can be DNA or RNA.

As used herein, the terms "treat", "treatment" and "treating" refer to the reduction or amelioration of the severity, duration and/or progression of a disease or disorder or one or more symptoms thereof resulting from the administration of one or more therapies. Such terms refer to a reduction in the replication of a fungus or bacteria, or a reduction in the spread of a fungus or bacteria to other organs or tissues in a subject or to other subjects.

The term "therapeutic agent" refers to a substance capable of producing a curative effect in a disease state. For example, a therapeutic agent for treating a subject having bacteremia is an antibiotic which include, but are not limited to, penicillins, cephalosporins, fluroquinolones, tetracyclines, macrolides, and aminoglycosides. A therapeutic agent for treating a subject having a viral respiratory infection includes, but is not limited to oseltamivir, RNAi antivirals, inhaled rhibovirons, monoclonal antibody respigams, zanamivir, and neuriminidase blocking agents. The invention contemplates the use of the methods of the invention to determine treatments with antivirals or antibiotics that are not yet available.

Furthermore, the methods of the invention may be used to screen compounds that are suspected to have antiviral properties. The methods may include a) determining first gene expression levels of genes from a first peripheral blood cell sample of a test subject, wherein the genes are specific for a particular respiratory virus, b) inoculating the test subject with influenza, c) determining second gene expression levels of the genes from a second peripheral blood cell sample of the test subject at a time later than step b) to determine the infection status of the test subject, d) administering the compound to the test subject infected with the respiratory virus and e) determining third gene expression levels of the genes from a third peripheral blood cell sample of the test subject at a time later than step d) to determine the infection status of the test subject. In some embodiments, cell lines may be used instead of test subjects. Accordingly, the methods described herein become the basis for high-throughput screening of compounds for antiviral activity. Such methods would be useful in identifying post-infectious therapeutics in the event of a pandemic viral outbreak.

The methods and assays of the invention may be based upon three different molecular platforms: RNA expression, metabolomic expression, and proteomic expression.

Gene expression patterns have been identified that can be used to characterize host response to viral infection, and to identify infected individuals with a high degree of accuracy. As shown in FIG. 1, the gene expression patterns for rhinovirus, RSV, and influenza A share a number of common genes, reflecting the common pathways affected by the host in response to viral respiratory infection. In particular, RSAD2 (viperin), a potential antiviral molecule, was found to be the most highly differentially expressed gene between infected and uninfected individuals at 48 hours post inoculation. RSAD2 (viperin) was a component of the rhinovirus (HRV-16) predictive factor and was selected by the probit regression model as the key differentially expressed gene in blood for determining infected state in the rhinovirus cohort. Similarly, whole blood gene expression studies looking at RSV infection in hospitalized infants contained similar differentially expressed genes to the RSV factors, with a predominance of interferon-response elements, FCγ1AR, and OAS3.

Overall, the following gene signatures are useful for determining the etiology of a respiratory viral infection, as well as the likelihood that the subject will become symptomatic: ATF3, CCL2, CXCL10, DDX58, ETV7, FCGR1A, FCGR1B, GBP1, HERC5, IFI27, IFI44, IFI44L, IFI6, IFIT1, IFIT2, IFIT3, IFIT5, INDO, ISG15, LAMP3, LAP3, LOC26010, LOC727996, LY6E, MS4A4A, MX1, OAS1, OAS2, OAS3, OASL, PML, RSAD2, RTP4, SEPT4, SERPING1, SIGLEC1, SOCS1, TNFAIP6, and XAF1. In particular, regulation of the following genes are involved in response to viral respiratory infection, generally, a.k.a. panviral infection. The panviral genes include: PANVIRAL: RSAD2, IFI44L, LAMP3, SERPING1, IFI44, IFIT1, IFI44, ISG15, SIGLEC1, OAS3, HERC5, LOC727996, IFIT3, IFI6, OASL, IFI27, ATF3, MX1, OAS1, LOC26010, XAF1, IFIT2, OAS2, LY6E, SEPT4, DDX58, TNFAIP6, RTP4, PML, CXCL10. Rhinovirus infection may be uniquely identified from other types of respiratory viral infection by measuring the regulation of the following genes: RSAD2, LAMP3, IFI44L, IFIT1, SIGLEC1, IFI44, OAS3, LOC727996, SERPING1, HERC5, ISG15, IFI6, IFI44, INDO, MX1, IFIT3, OASL, LOC26010, OASL, CXCL10, ATF3, OAS1, DDX58, OAS1, LY6E, OAS2, CCL2, XAF1, IFIT2, and SOCS1. Respiratory Syncytial Virus (RSV) infection may be uniquely identified from other types of respiratory viral infection by measuring the regulation of the following genes: RSAD2, SERPING1, IFI44L, IFIT1, IFI44, LAMP3, OAS3, HERC5, ISG15, IFIT3, SIGLEC1, OASL, OAS1, LOC26010, MX1, IFI6, FCGR1A, GBP1, ATF3, IFIT5, LAP3, OASL, IFIT2, RTP4, GBP1, DDX58, ETV7, FCGR1B, and OAS1. Influenza A infection may be uniquely identified from other types of respiratory viral infection by measuring the regulation of the following genes: RSAD2, IFI44L, SIGLEC1, LAMP3, IFIT1, IFI44, SERPING1, IFI27, ISG15, HERC5, LOC26010, IFI6, LOC727996, IFIT3, OAS3, OASL, SEPT4, XAF1, OAS1, LY6E, MS4A4A, SIGLEC1, TNFAIP6, CCL2, OAS1, MX1, TNFAIP6, RTP4, and OASL.

Alterations in gene, protein and metabolite expression in blood in response to pathogen exposure are the basis for screening tests of the invention. Human models of pathogen exposure exist and murine models of bacterial and viral respiratory infections are well established and are an ideal means for defining gene expression patterns that are host "signatures" of the infectious prodrome. Murine and human data from peripheral blood may be used as a diagnostic window into host response to infectious challenges. Using this data, combined with literature markers, a Bayesian predictive model was established. Bayesian modeling techniques are described in U.S. patent application Ser. No. 10/692,002 which is incorporated by reference herein in its entirety.

The methods and assays of the invention may be based upon RNA expression. RNA from whole blood from humans and mice can be collected using PAXgene™ RNA tubes (PreAnalytiX, Valencia, Calif.). The RNA can be extracted using a standard Versagene™ (Gentra Systems, Inc, Minneapolis, Minn.) RNA extraction protocol. The Versagene™ kit produces greater yields of higher quality RNA from the PAXgene™ RNA tubes. Following RNA extraction, we can use GLOBINClear™ (Ambion, Austin, Tex.) for whole blood globin reduction. (This method uses a bead-oligonucleotide construct to bind globin mRNA and, in our experience, we are able to remove over 90% of the globin mRNA.) Quality of the RNA can be assessed by several means. First, RNA quality can be assessed using an Agilent 2100 Bioanalyzer immediately following extraction. This analysis provides an RNA Integrity Number (RIN) as a quantitative measure of RNA quality. Second, following globin reduction, the samples can be compared to the globin-reduced standards. Finally, the scaling factors and background can be assessed following hybridization to the microarrays. Processed RNA can be undergo automated cRNA probes production and hybridization using the Affymetrix GeneChip™ TM High Throughput (HT) Array System for whole-genome transcript analysis. The Affymetrix HT A system uses the Affymetrix U133A gene set of over 22,000 separate transcripts. As an alternative to RNA arrays, real time PCR can be used to quickly identify gene expression from a whole blood sample. For example, the isolated RNA can be reverse transcribed and then amplified and detected in real time using non-specific fluorescent dyes that intercalate with the resulting ds-DNA, or sequence-specific DNA probes labeled with a fluorescent reporter which permits detection only after hybridization of the probe with its complementary DNA target.

Thus, the invention enables a method of identifying a subject infected with a respiratory virus comprising a) determining gene expression levels of at least three genes from a peripheral blood cell sample of the subject, wherein the genes are selected from the group consisting of ATF3, CCL2, CXCL10, DDX58, ETV7, FCGR1A, FCGR1B, GBP1, HERC5, IFI27, IFI44, IFI44L, IFI6, IFIT1, IFIT2, IFIT3, IFIT5, INDO, ISG15, LAMP3, LAP3, LOC26010, LOC727996, LY6E, MS4A4A, MX1, OAS1, OAS2, OAS3, OASL, PML, RSAD2, RTP4, SEPT4, SERPING1, SIGLEC1, SOCS1, TNFAIP6, and XAF1, and b) comparing the gene expression levels of the genes to standard gene expression levels for the genes. In some embodiments, the screening may be for panviral respiratory infection, rhinovirus, RSV, influenza A, or a combination thereof.

The standard gene expression levels for the genes are the average expression levels of the genes for a non-infected population to which the subject belongs, e.g., adult American female, or for a particular subject prior to being infected. A difference between the levels of expression of the genes and the standard gene expression levels is indicative of a subject infected with a respiratory virus. For example, a peripheral blood sample may be obtained from a subject at a medical laboratory, the blood sample worked up and screened for gene expression, the results of the screening compared to the gene expression standards, and the subject informed of her infectious status.

After the infectious status of the subject has been determined, she may undergo treatment, for example anti-virals, and/or she may be quarantined to her home for the course of the infection. The invention will prove particularly valuable in screening subjects in populations that are in close-contact with one another and prone to outbreaks, such as the population of a college campus.

The person performing the peripheral blood sample need not perform the comparison, however, as it is contemplated that a laboratory may communicate the gene expression levels to a medical practitioner for the purpose of identifying a subject infected with a respiratory virus. Additionally, it is contemplated that a medical professional, after examining a patient, would order an agent to obtain a peripheral blood sample, have the sample screened for gene expression and compared to standard values, and have the agent report patient's infection status to the medical professional. Once the medical professional has obtained the patient's infection status, the medical professional could order suitable treatment and/or quarantine.

In order to complete the comparison, the invention contemplates a computer readable medium comprising standard gene expression levels of least three genes selected from the group consisting of ATF3, CCL2, CXCL10, DDX58, ETV7, FCGR1A, FCGR1B, GBP1, HERC5, IFI27, IFI44, IFI44L, IFI6, IFIT1, IFIT2, IFIT3, IFIT5, INDO, ISG15, LAMP3, LAP3, LOC26010, LOC727996, LY6E, MS4A4A, MX1, OAS1, OAS2, OAS3, OASL, PML, RSAD2, RTP4, SEPT4, SERPING1, SIGLEC1, SOCS1, TNFAIP6, and XAF1 and responsivity information indicating changes in the gene expression levels of the at least three genes when a subject is infected with a respiratory virus. In other embodiments, the computer readable medium may have gene sets and responsivity data specific for rhinovirus infections, respiratory syncytial virus infections, and influenza infections. The invention additionally contemplates a computer readable medium comprising standard protein expression levels of least three proteins selected from the group consisting of AFAM, ACTG, LUM, AACT, SAMP, FHR1, APOH, HRG, APOA4, A2GL, CFAB, CO7, APOB, KAIN, CHLE, APOE, ITIH4, Myeloperoxidase, MMP-2, Myoglobin, and IgE.

It is to be understood that the invention is not limited in its application to the details of construction and the arrangement of components set forth in the following description or illustrated in the following drawings. The invention is capable of other embodiments and of being practiced or of being carried out in various ways.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any nonclaimed element as essential to the practice of the invention.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

Further, no admission is made that any reference, including any patent or patent document, cited in this specification constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinency of any of the documents cited herein.

EXAMPLES

Example 1

Genomic Signatures to Identify Symptomatic Respiratory Viral Infection

Three human viral challenge cohorts were used for rhinovirus, respiratory syncytial virus, and influenza A. Each cohort was used to develop a robust blood mRNA expression signature that classifies symptomatic human respiratory viral infection. Factor analysis of mRNA expression data revealed a "panviral" bio-signature of disease encompassing transcripts of genes known to be related to viral infection and the overall immune response. Signatures for rhinovirus, respiratory syncytial virus, and influenza A infection were also developed.

Human Rhinovirus Cohort (n=20): Healthy volunteers were recruited via advertisement to participate in the rhinovirus challenge study through an active screening protocol at the University of Virginia (Charlottesville, Va.). The protocol was approved by the Human Investigations Committee of the University of Virginia, the Institutional Review Board of Duke University Medical Center, and the SSC-SD Institutional Review Board (US Department of Defense; Washington, D.C.). Subjects who met inclusion criteria underwent informed consent and pre-screening for serotype-specific anti-rhinovirus approximately two weeks prior to study start date. On the day prior to inoculation, subjects underwent repeat rhinovirus antibody testing as well as baseline laboratory studies, including complete blood count, serum chemistries, and hepatic enzymes. On day of inoculation, $10^6$ TCID$_{50}$ GMP rhinovirus (Johnson and Johnson, New Brunswick, N.J.) was inoculated intranasally according to previously published methods. Subjects were admitted to the quarantine facility for 48 hours following rhinovirus inoculation and remained in the facility for 48 hours following inoculation. Blood was sampled into RNA PAXGene™ blood collection tubes (PreAnalytix; Franklin Lakes, N.J.) at pre-determined intervals post inoculation. Nasal lavage samples were obtained from each subject daily for rhinovirus titers to accurately gauge the success and timing of the rhinovirus inoculation. Following the 48$^{th}$ hour post inoculation, subjects were released from quarantine and returned for three consecutive mornings for sample acquisition and symptom score ascertainment.

Based on the criteria described above, the attack rate for Rhinovirus was 50%, as ten of the 20 inoculated subjects developed upper respiratory infection-like symptoms and had confirmed viral shedding. Peak symptoms occurred at 48 hours (n=2), 72 hours (n=4) or 96 hours (n=4) post inoculation (median 72 hours).

Human RSV Cohort (n=20): A healthy volunteer intranasal challenge with RSV A was performed in a manner similar to the rhinovirus intranasal challenge. The protocol was approved by the East London and City Research Ethics Committee 1 (London, UK), an independent institutional review board (WIRB: Western Institutional Review Board, Olympia Wash.), the Institutional Review Board of Duke University Medical Center (Durham, N.C.), and the SSC-SD Institutional Review Board (US Department of Defense, Washington, D.C.). The RSV challenge was performed by Retroscreen Virology, Ltd (London, UK) in 20 pre-screened volunteers who provided informed consent. All subjects underwent informed consent. On day of inoculation, a dose of $10^4$ TCID$_{50}$ respiratory syncytial virus (RSV; serotype A) manufactured and processed under current good manufacturing practices (cGMP) by Meridian Life Sciences, Inc. (Memphis, Tenn. USA) was inoculated intranasally per standard methods. Blood and nasal lavage collection methods were similar to the rhinovirus cohort, but continued throughout the duration of the quarantine. Due to the longer incubation period of RSV A, subjects were not released from quarantine until after the 288$^{th}$ hour AND were negative by rapid RSV antigen detection (BinaxNow Rapid RSV Antigen; Inverness Medical Innovations, Inc).

Based on the criteria described above, the attack rate for Respiratory Syncytial Virus (RSV) was 42%, as eight of the 20 inoculated subjects developed upper respiratory infection-like symptoms and had confirmed viral shedding. Peak symptoms occurred at 93.5 hours (n=1), 117.5 hours (n=1), 141.5 hours (n=5) and 165.5 hours (n=1) post inoculation (median 141.5 hours).

Influenza Cohort (n=17): A healthy volunteer intranasal challenge with influenza A, A/Wisconsin/67/2005 (H3N2) was performed at Retroscreen Virology, Ltd (Brentwood, UK) in 17 pre-screened volunteers who provided informed consent. On day of inoculation, a dose of $10^6$ TCID$_{50}$ Influenza A manufactured under current good manufacturing practices (cGMP) by Baxter BioScience, (Vienna, Austria) was diluted and inoculated intranasally per standard methods at a varying dose (1:10, 1:100, 1:1000, 1:10000) with four to five subjects receiving each dose. Due to the longer incubation period of influenza as compared to rhinovirus, subjects were not released from quarantine until after the 168th hour. Blood and nasal lavage collection continued throughout the duration of the quarantine. All subjects received oral oseltamivir (Roche Pharmaceuticals) 75 mg by mouth twice daily prophylaxis at day 6 following inoculation. All patients were negative by rapid antigen detection (BinaxNow Rapid Influenza Antigen; Inverness Medical Innovations, Inc) at time of discharge.

Based on the criteria described above, the attack rate for influenza A was 53%, as nine of the 17 inoculated subjects developed upper respiratory infection-like symptoms and had confirmed viral shedding. Peak symptoms occurred at 50 hours (n=1), 62 hours (n=2), 74 hours (n=2), 86 hours (n=2), 98 (n=1) and 110 hours (n=1) post inoculation (median 80 hours).

Case Definitions: Symptoms were recorded twice daily using standardized symptom scoring (Jackson et al., 1958). The modified Jackson Score requires subjects to rank symptoms of upper respiratory infection (stuffy nose, scratchy throat, headache, cough, etc) on a scale of 0-3 of "no symptoms," "just noticeable," "bothersome but can still do activities," and "bothersome and cannot do daily activities." For all cohorts, modified Jackson scores were tabulated to determine if subjects became symptomatic from the respiratory viral challenge. A modified Jackson score of >=6 over the quarantine period was the primary indicator of successful viral infection (Turner, 2001) and subjects with this score were denoted as "symptomatic, infected." Viral titers from daily nasopharyngeal washes were used as corroborative evidence of successful infection using quantitative culture (rhinovirus, RSV, influenza).

Subjects were classified as "asymptomatic, not infected (healthy)" if the Jackson score was less than 6 over the five days of observation and viral shedding was not documented after the first 24 hours subsequent to inoculation. Standardized symptom scores tabulated at the end of each study to determine attack rate and time of maximal symptoms (time "T").

Biological Sample Collections: For each viral challenge, subjects had the following samples taken 24 hours prior to inoculation with virus (baseline), immediately prior to inoculation (pre-challenge) and at set intervals following challenge: peripheral blood for serum and plasma, peripheral blood for RNA PAXgene™, nasal wash for viral culture/PCR, urine, and exhaled breath condensate. For the rhinovirus challenge, peripheral blood was taken at baseline, then at 4 hour intervals for the first 24 hours, then 6 hour intervals for the next 24 hours, then 8 hour intervals for the next 24 hours and then 24 hour intervals for the remaining 3 days of the study. For the RSV and influenza challenges, peripheral blood was taken at baseline, then at 8 hour intervals for the initial 120 hours and then 24 hours for two further days. For all challenge cohorts, nasopharyngeal washes, urine and exhaled breath condensates were taken at baseline and every 24 hours. Samples were aliquoted and frozen at −80° C. immediately.

The study focused on comparison of baseline samples with RNA PAXgene™ samples taken at time of peak symptoms. Paxgene™ RNA from the timepoint of maximal symptoms was chosen for hybridization to Affymetrix U133a human microarrays for further analysis. For all results reported, gene expression signatures were evaluated at the time of maximal symptoms following viral inoculation for symptomatic subjects and a matched timepoint for asymptomatic subjects. Baseline (pre-inoculation) samples were also analyzed for all subjects.

RNA purification and microarray analysis: RNA was extracted by an independent laboratory (Expression Analysis, Durham, N.C.) from whole blood using the PAXgene™ 96 Blood RNA Kit (PreAnalytiX, Valencia, Calif.) employing the manufacturer's recommended protocol. The samples were removed from −80° C. and incubated at room temperature for 2 hr to ensure complete lysis. Following lysis, the tubes were centrifuged for 10 min at 5,000×g, the supernatant was decanted, and 4 ml of RNase-free water was added to the pellet. The tube was vortexed to thoroughly resuspend the pellet and centrifuged for 10 min at 5000×g, and the entire supernatant was discarded. The remaining pelleted lysate was resuspended in 350 µl of buffer BR1 by vortexing, added to microcentrifuge tubes containing 40 µl of Proteinase K and 300 µl of buffer BR2, then incubated for 30 min at 65° C. Following incubation, the specimens were transferred to a PAXgene 96 Filter Plate and centrifuged at 5600×g for 10 min. Three hundred fifty microliters of 100% ethanol was added to the eluate from the filter plate and mixed by gentle pipetting. The entire volume was then transferred to a PAXgene 96 RNA plate with negative pressure applied via vacuum manifold. The plate was then washed by adding 500 µl of buffer BR3 per well under negative pressure. Eighty microliters DNase I incubation mix was added directly to the PAXgene membrane, then allowed to incubate at room temperature and pressure. Following DNase I digestion, the plate was washed with successive applications of 500 µl buffer BR3 and 1 ml BR4 with negative pressure. A final volume of 1 ml of buffer BR4 was added to each membrane, then the plate was centrifuged at 5600×g for 10 min to ensure the membranes were completely dry. RNA was eluted in two applications of 45 µL buffer BR5 via centrifugation at 5600×g for 4 min for each elution. RNA was quantified via UV spectrophotometer, and quality confirmed via the Agilent 2100 Bioanalyzer (Agilent; Santa Clara, Calif.).

Hybridization and microarray data collection was performed by a third party laboratory (Expression Analysis, Durham, N.C.) using the GeneChip™® Human Genome U133A 2.0 Array (Affymetrix, Santa Clara, Calif.). The arrays used for gene quantitation contain probes for approximately 18,400 transcripts and variants, including over 14,500 well-characterized human genes. The sequences from which these probe sets were derived were selected from GenBank, dbEST, and RefSeq. The sequence clusters were created from the UniGene database (Build 133, Apr. 20, 2001) and then refined by analysis and comparison with a number of other publicly available databases, including the Washington University EST trace repository and the University of California, Santa Cruz Golden-Path human genome database (April 2001 release). Some gene sequences were selected from GenBank, dbEST, and RefSeq. Sequence clusters were created from the UniGene database (Build 159, Jan. 25, 2003) and refined by analysis and comparison with a number of other publicly available databases, including the Washington University EST trace repository and the NCBI human genome assembly (Build 31).

Each target was prepared and hybridized according to the Affymetrix Technical Manual. Total RNA (2.5 µg) was converted into cDNA using Reverse Transcriptase (Invitrogen) and a modified oligo(dT)24 primer that contains T7 promoter sequences (GenSet). A set of four peptide nucleic acid (PNA) oligomers (Applied Biosystems; Foster City, Calif.) with sequences complimentary to globin mRNA were added to reduce globin RNA transcription. After first strand synthesis, residual RNA was degraded by the addition of RNaseH, and a double stranded cDNA molecule was generated using DNA Polymerase I and DNA Ligase. The cDNA was then purified and concentrated using a phenol:chloroform extraction followed by ethanol precipitation. The cDNA products were incubated with T7 RNA Polymerase and biotinylated ribonucleotides using an In Vitro Transcription kit (Affymetrix). The resultant cRNA product was purified using an RNeasy column (QIAGEN) and quantified with a spectrophotometer.

The cRNA target (20 µg) was incubated at 94° C. for 35 min in fragmentation buffer (Tris, MgOAc, KOAc). The fragmented cRNA was diluted in hybridization buffer (MES, NaCl, EDTA, Tween 20, Herring Sperm DNA, Acetylated BSA) containing biotin-labeled OligoB2 and Eukaryotic Hybridization Controls (Affymetrix). The hybridization cocktail was denatured at 99° C. for 5 min, incubated at 45° C. for 5 min, and then injected into a GeneChip™ cartridge. The GeneChip™ array was incubated at 42° C. for at least 16 hr in a rotating oven at 60 rpm. GeneChips™ were washed with a series of nonstringent (25° C.) and stringent (50° C.) solutions containing variable amounts of MES, Tween20 and SSPE. The microarrays were then stained with Streptavidin Phycoerythrin and the fluorescent signal was amplified using a biotinylated antibody solution. Fluorescent images were detected in an GeneChip™ Scanner 3000 and expression data was extracted using the GeneChip™ Operating System v 1.1 (Affymetrix). All GeneChips™ were scaled to a median intensity setting of 500.

Statistical Analysis: Following RMA normalization of raw probe data, sparse latent factor regression analysis was applied to each dataset. See, e.g., Carvalho et al., "High dimensional sparse factor modeling: applications in gene expression genomics," *Journal of American Statistical Association* (2008), incorporated herein by reference in its entirety. This reduces the dimensionality of the complex gene expression array dataset assuming that many of the probe sets on the expression array chip are highly interrelated (targeting the same genes or genes in the same pathways). Dimension reduction is performed by constructing factors (groups of genes with related expression values). These factors are used in a sparse linear regression framework to explain the variation seen in all of the probe sets. By default, most of the coefficients in this linear regression are zero. Thus, a small number (e.g., 20) of factors explain variation seen in any single dataset.

Factor loadings are defined as the coefficients of the factor regression, and, to explore the biological relevance any particular factor, we examine the genes that are "in" that factor—the genes that show significantly non-zero factor loadings. "Factor scores" are defined as the vector that best describes the co-expression of the genes in a particular factor. Both factor loadings and factor scores are fit to the data concurrently, and the full details of the process can be found in the supplementary statistical analysis section. While 20 factors were used for the results reported here, we also considered 30 and 40, with minimal effect on the significant factor loadings. Notably, the initial models built to determine factors that distinguish symptomatic infected individuals from asymptomatic individuals were derived using an unsupervised process (i.e., the model classified subjects based on gene expression pattern alone, without a priori knowledge of infection status).

The top 30 genes in each factor were used as features for the sparse probit regression model to perform leave-one-out cross validation and generate ROC curves to estimate performance of the algorithm. The probit regression model selects the "top" predictive gene from the gene set for sample classification and generation of an ROC curve. Validation of the factor most discriminative between the asymptomatic and symptomatic state was performed using labeled data. Validation between datasets (rhinovirus, RSV, and influenza A) was performed by training the regression model on one set of data (i.e. one viral exposure) and using this model to predict health or disease in a different data set (i.e. a different viral exposure). Validation of the model using the publicly available dataset was performed by utilizing the joint factor analysis on the viral exposure dataset (rhinovirus, RSV, and influenza), building a probit classifier using the top 30 genes from the most predictive factor and applying this classifier to the publicly available dataset to estimate the predictive performance of the panviral classifier.

Data from each challenge (rhinovirus, RSV, influenza) was combined and analyzed as a single dataset. Eighty-four timepoints were included in the analysis (rhinovirus: 10 baseline, 10 symptomatic, 10 matched timepoint asymptomatic; RSV: 10 baseline, 9 symptomatic, 10 matched timepoint asymptomatic; influenza: 8 baseline, 9 symptomatic, 8 matched timepoint asymptomatic). Twenty factors were developed using all available probes, and a single factor (Factor 16) emerged as best able to discriminate symptomatic (infected) subjects (rhinovirus, RSV or influenza A) from asymptomatic (uninfected) individuals. Baseline (pre-inoculation) gene expression was indistinguishable from the matched timepoint of asymptomatic subjects. Baseline gene expression in subjects who became symptomatic was indistinguishable from those who remained asymptomatic. The top 30 predictive genes contained in Factor 16 are known to characterize host response to viral infection, and included RSAD2, the OAS family, interferon response elements and the myxovirus-resistance gene MX1. These 30 genes were used as features for the sparse probit regression model to perform leave-one-out cross validation and generate an ROC curve to estimate performance of the model. Leave-one-out cross validation correctly identified 96.5% of infected subjects (misclassification rate 3.5%, 3/84). These data—from three distinct viral challenge experiments—demonstrate a clear panviral response factor as a common feature of peak infection.

Figure 2:
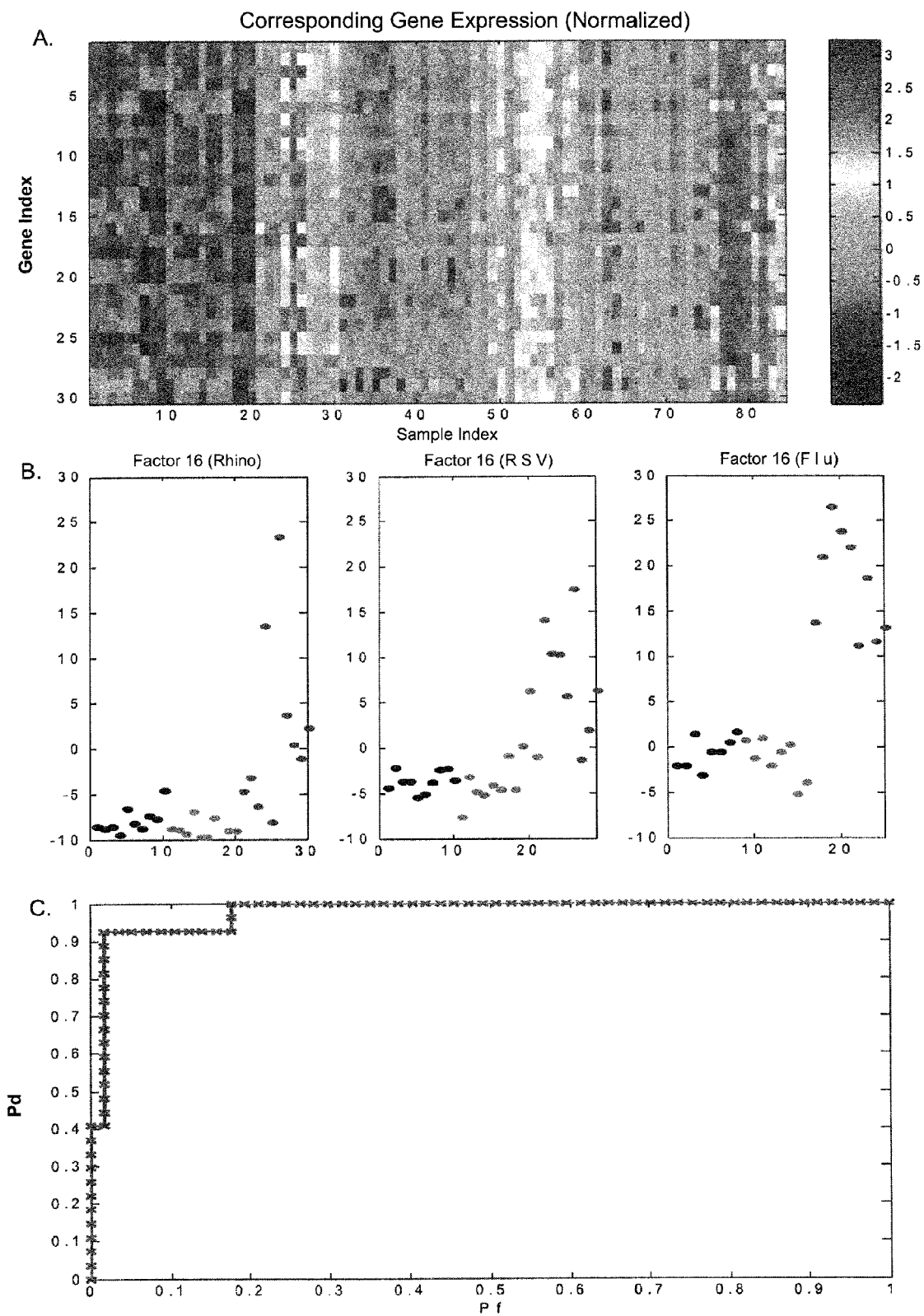
FIG. 2 shows a panviral gene expression signature of symptomatic respiratory viral infection.

The results of the sparse probit regression model are shown in FIG. 2, which shows a panviral gene expression signature of symptomatic respiratory viral infection. FIG. 2 A) shows a heat map representing gene expression for genes contained in Factor 16. Columns represent subjects and correspond to the points in FIG. 2 B), with the first 10 columns representing baseline gene expression of asymptomatic individuals in the rhinovirus challenge, the next 10 columns representing timepoints matched to peak symptoms for the asymptomatic subjects in the rhinovirus cohort and the following 10 columns representing time of peak symptoms for the 10 subjects who developed symptomatic rhinovirus infection. A similar layout continues for the RSV and influenza cohorts. Blue and red represent extremes of gene expression, with visually apparent differences between baseline and matched timepoints in the asymptomatic individuals versus time of peak symptoms in symptomatic individuals. The initial models were built without label information for each subject (asymptomatic versus symptomatic, baseline timepoint versus infected/matched timepoint). Such a design allows for the model to cluster individuals based on expression patterns alone, thus minimizing bias in factor organization. FIG. 2 B) shows factor plots representing categorization of asymptomatic and symptomatic subjects at baseline (black), matched timepoint to peak symptoms (asymptomatic, red) and peak symptoms (symptomatic, blue). FIG. 2 C) shows leave-one-out cross validation correctly identifies 97% of individuals with viral infection versus no infection (3/84 misclassified). Pd=probability of detection; Pf=probability of false discovery.

Figure 3:
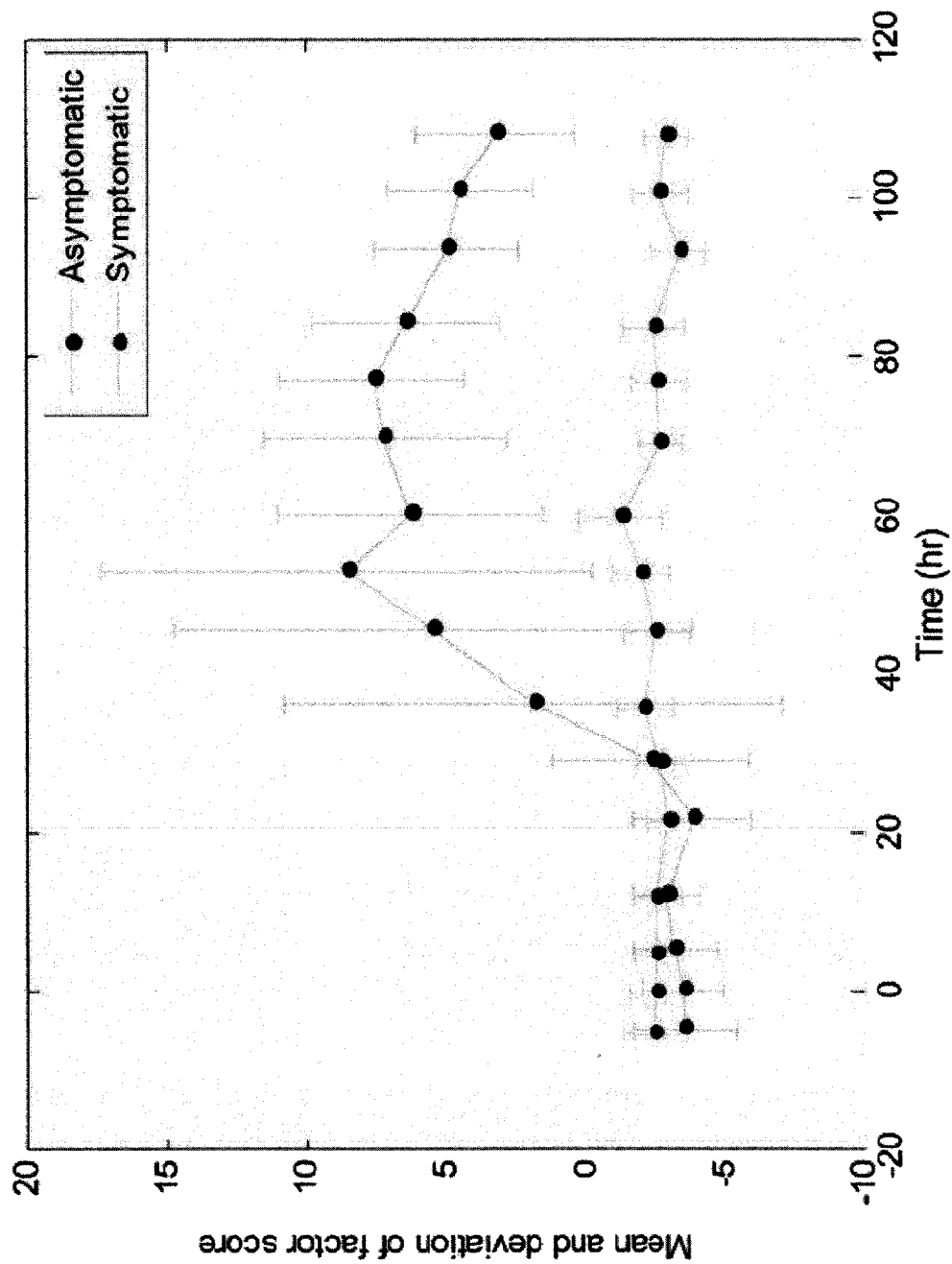
FIG. 3 shows that individuals infected with influenza can be reliably detected at 40 hours post-inoculation, prior to the onset of symptoms.

The predictive power of the Factor 16 screening is better illustrated in FIG. 3, which shows Factor 16 trajectory for the acute respiratory viral factor described above for the symptomatic (blue) and asymptomatic (red) subjects from the influenza challenge study. Notably, factor 16 is detectable prior to the timing of peak symptoms, approximately 80 hours after infection. Each point represents the average factor score for the samples that fall into that group, with error bars representing the SD. For example, the blue dot at time 0 represents all samples from subjects immediately post-inoculation who will subsequently become symptomatic (nine subjects). A t test was performed at teach time point for difference in factor score from those who will become symptomatic and from those who will remain asymptomatic. The difference between factor scores for symptomatic and asymptomatic became significant at p<0.03 at 45.5 hr and continued through the end of the measurements. *p<0.03.

Figure 4:
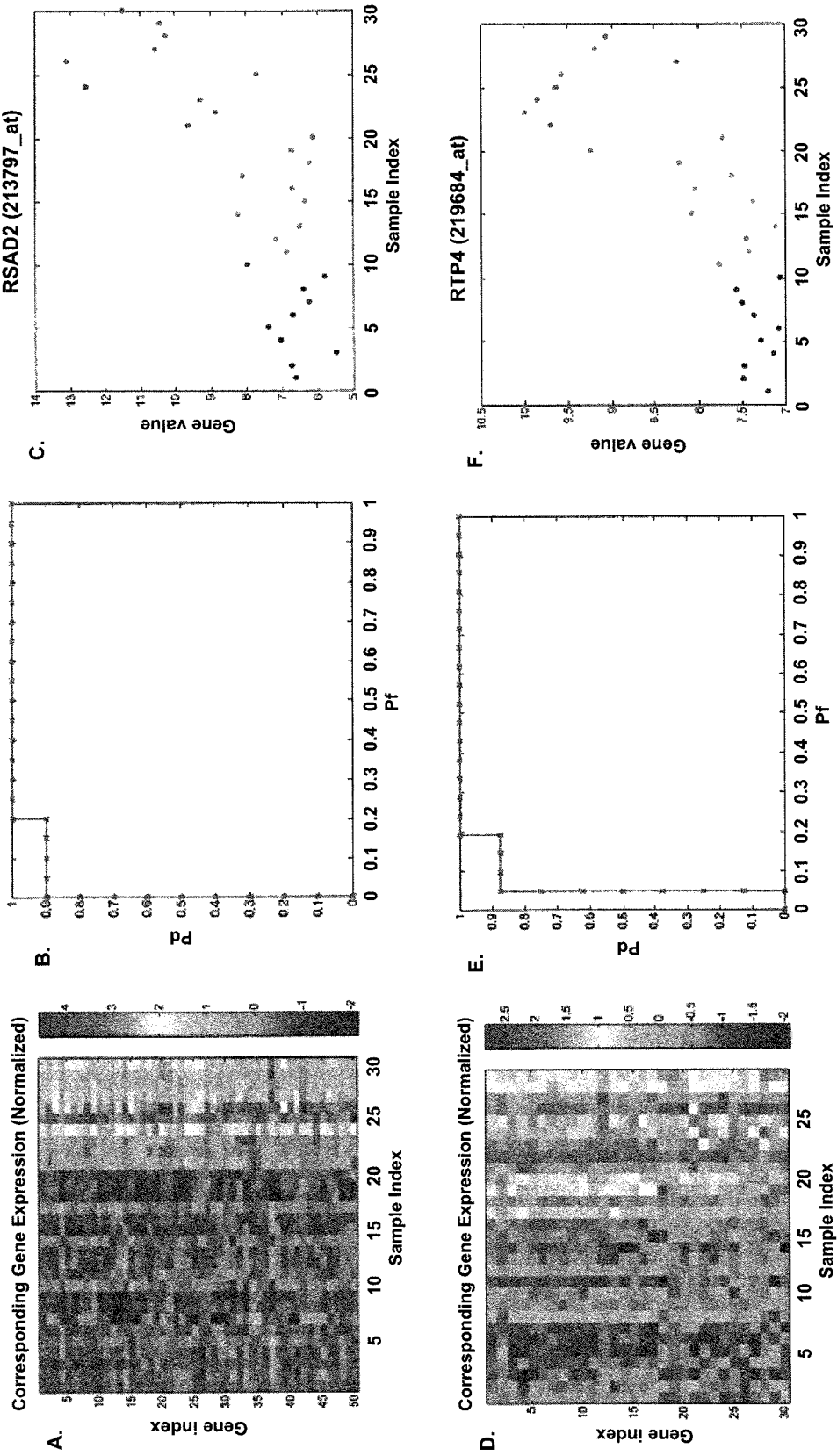
FIG. 4 shows peripheral blood gene expression signatures which differentiate adults with symptomatic respiratory tract infection from asymptomatic adults.
Figure 4:
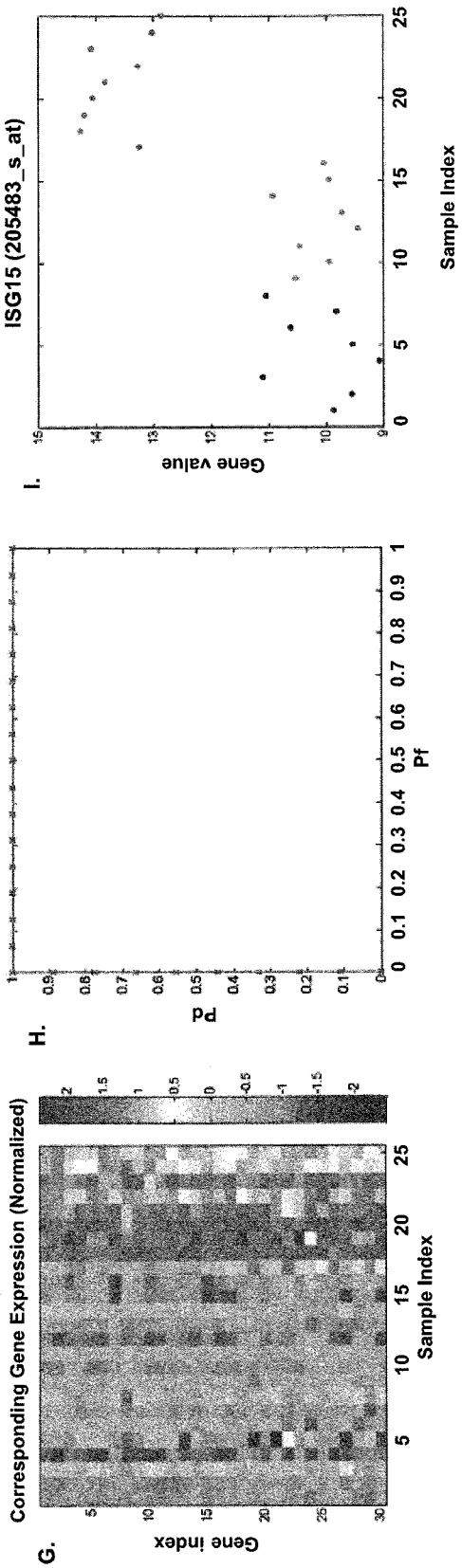

To further validate the robust panviral response signature, each dataset (rhinovirus, RSV and influenza A) was analyzed separately to identify a factor that characterized symptomatic viral infection for each individual dataset (FIG. 4). Sparse probit regression was performed on the 30 genes with the highest factor loading values in each factor, and this data was used for leave-one-out cross validation and generation of an ROC curve to estimate factor performance. Notably, the p-values associated with each factor (i.e. the likelihood that this group of genes would not be selected randomly) were $2.33 \times 10^{-5}$ (rhinovirus), $2.29 \times 10^{-7}$ (RSV), and $4.95 \times 10^{-13}$ (influenza) (www.gather.duke.edu).

FIG. 4 shows peripheral blood gene expression signatures which differentiate adults with symptomatic respiratory tract infection from asymptomatic adults. Internal cross-validation was performed between each viral challenge dataset. For each individual dataset (rhinovirus, RSV, or influenza A), baseline (pre-inoculation) gene expression was indistinguishable from the matched timepoint of asymptomatic subjects indicating that the state of 'health' defined by gene expression at baseline prior to inoculation was similar to a state of health post inoculation in subjects whom did not develop symptoms. FIG. 4 A) shows a heat map representing relative gene expression of genes in Factor 6 (rhinovirus). Blue indicates low expression levels and red high expression levels. Samples are arranged along the x axis, corresponding to baseline, asymptomatic and symptomatic and correspond linearly with points in FIG. 4 C). Notably, genes contained in this factor are known to be involved in host defense against viral infection, including interferon signaling (10 genes), host-viral interaction such as MX1, and the 2'-5' oligo (A) synthetase (OAS) gene family and viral sensing mechanisms (DDX58). FIG. 4 B) shows ROC curve for prediction of symptomatic versus asymptomatic subjects in the rhinovirus cohort, generated from probit function utilizing the top 30 genes in Factor 6. FIG. 4 C) shows the performance of the gene with the top factor loading score (RSAD2) at discriminating baseline (black), asymptomatic (red) and symptomatic (blue) subjects with experimental rhinovirus infection.

FIG. 4 D) shows a heat map representing relative gene expression of genes in Factor 20 (RSV). Blue indicates low expression levels and red high expression levels. Samples are arranged along the x axis, corresponding to baseline, asymptomatic and symptomatic and correspond linearly with points in FIG. 4 F). Genes contained in this discriminant factor include interferon-response genes (e.g. IFI44, IFIT1, IFIT3), the OAS family, and viral defense genes such as MX1 and RSAD2(Proud et al., 2008). FIG. 4 E) shows ROC curve for prediction of symptomatic versus asymptomatic subjects in the RSV cohort, generated from probit function utilizing the top 30 genes in Factor 20. FIG. 4 F) shows the performance of the gene with the top factor loading score (RTP4) at discriminating baseline (black), asymptomatic (red) and symptomatic (blue) subjects with experimental RSV infection.

FIG. 4 G) shows a heat map representing relative gene expression of genes in Factor 6 (Influenza). Blue indicates low expression levels and red high expression levels. Samples are arranged along the x axis, corresponding to baseline, asymptomatic and symptomatic and correspond linearly with points in FIG. 4 I). Genes contained in this discriminant factor include interferon-response genes (e.g. IFI44, IFI44L), SIGLEC1 (a sialoadehesin involved in monocyte response to interferon), the OAS family, and viral defense genes such as MX1 and RSAD2. FIG. 4 H) shows ROC curve for prediction of symptomatic versus asymptomatic subjects in the influenza cohort, generated from probit function utilizing the top 30 genes in Factor 6. FIG. 4 I) shows the performance of the gene with the top factor loading score (ISG15) at discriminating baseline (black), asymptomatic (red) and symptomatic (blue) subjects with experimental RSV infection.

The individual challenge-specific factors were used as a de facto "training set" to classify subjects from the other viral challenges. When the model was trained on any individual dataset, prediction of symptomatic versus asymptomatic was >96%. This cross-validation supports the conclusion that, at peak viral respiratory infection symptoms, the host response converges to encompass a gene expression program highly characteristic of response to viral infection. Overlap between genes represented in the panviral illness factor and individual factors were shown in FIG. 1. Notably, genes represented in these factors were highly representative of host response to viral infection, including RSAD2, interferon response elements and the OAS gene family. TABLE 1 lists the gene sets corresponding to each respiratory virus, as well as the genes common to viral respiratory illness (panviral).

TABLE 1

Gene sets of Rhinovirus, RSV, and Influenza whose variance is indicative of infection with the respective virus.

| RHINOVIRUS | RSV | INFLUENZA | PANVIRAL |
|---|---|---|---|
| RSAD2 | RSAD2 | RSAD2 | RSAD2 |
| LAMP3 | SERPING1 | IFI44L | IFI44L |
| IFI44L | IFI44L | SIGLEC1 | LAMP3 |
| IFIT1 | IFIT1 | LAMP3 | SERPING1 |
| SIGLEC1 | IFI44 | IFIT1 | IFI44 |
| IFI44 | IFI44 | IFI44 | IFIT1 |
| OAS3 | LAMP3 | SERPING1 | IFI44 |
| LOC727996 | OAS3 | IFI27 | ISG15 |
| SERPING1 | HERC5 | ISG15 | SIGLEC1 |
| HERC5 | ISG15 | IFI44 | OAS3 |
| ISG15 | IFIT3 | HERC5 | HERC5 |
| IFI6 | SIGLEC1 | LOC26010 | LOC727996 |
| IFI44 | OASL | IFI6 | IFIT3 |
| INDO | OAS1 | LOC727996 | IFI6 |
| MX1 | LOC26010 | IFIT3 | OASL |
| IFIT3 | MX1 | OAS3 | IFI27 |
| OASL | IFI6 | OASL | ATF3 |
| LOC26010 | FCGR1A | SEPT4 | MX1 |
| OASL | GBP1 | XAF1 | OAS1 |
| CXCL10 | ATF3 | OAS1 | LOC26010 |
| ATF3 | IFIT5 | LY6E | XAF1 |
| OAS1 | LAP3 | MS4A4A | IFIT2 |
| DDX58 | OASL | SIGLEC1 | OAS2 |
| OAS1 | IFIT2 | TNFAIP6 | LY6E |
| LY6E | RTP4 | CCL2 | SEPT4 |
| OAS2 | GBP1 | OAS1 | DDX58 |
| CCL2 | DDX58 | MX1 | TNFAIP6 |
| XAF1 | ETV7 | TNFAIP6 | RTP4 |
| IFIT2 | FCGR1B | RTP4 | PML |
| SOCS1 | OAS1 | OASL | CXCL10 |

The Panviral gene set can be used to distinguish a viral origin of respiratory distress.

This study showed the ability to detect viral infection early, e.g., prior to the development of symptoms, such as runny nose, sneezing, earache, cough, shortness of breath, malaise, myalgias, headache, stuffy nose, sore throat.

Example 2

Protein Signatures to Identify Symptomatic Respiratory Viral Infection

Figure 6:
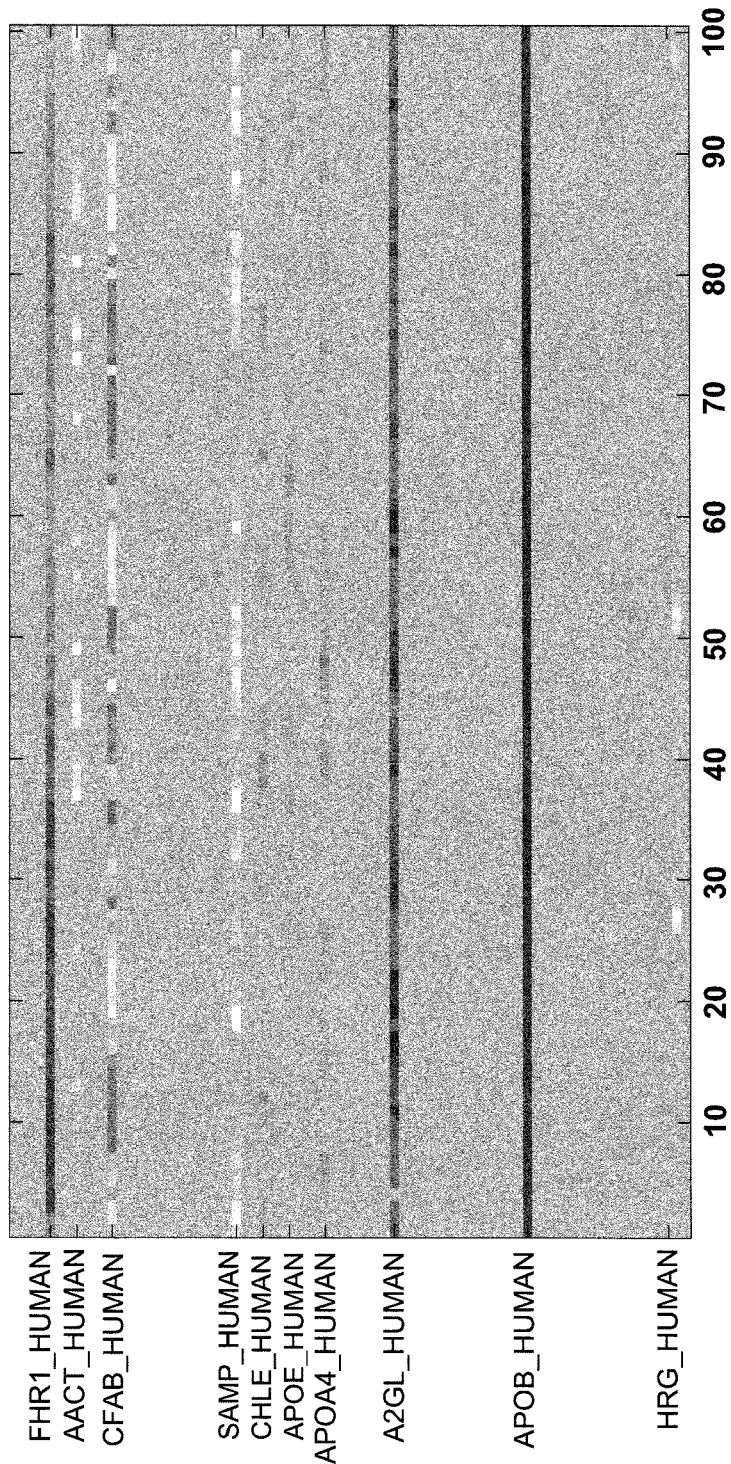
FIG. 6 shows protein signatures used for identifying respiratory viral infections.

Based upon the genetic data identified in EXAMPLE 1, a test for the identification of respiratory infection using some of the proteins encoded by the genes of TABLE 1 was developed. A heat map representing protein expression of proteins coded by the genes of Factor 6 (influenza) is shown in FIG. 6.

A peripheral blood sample of a subject known to have been infected with H1N1 influenza was screened with LC/MS to determine the expression levels of the listed proteins. As shown in FIG. 6, the proteins were expressed at elevated levels compared to standard levels for a population that was not infected with influenza. This EXAMPLE demonstrates the conservation of protein expression between influenza strains, because the standards were derived from the H3N2 studies, described above in EXAMPLE 1.

Example 3

Correlation of Genetic Markers to Infection in Literature Cohort

Given the strong viral response signature that distinguished symptomatic rhinovirus, RSV, and influenza infection from uninfected subjects, the specificity of this response to viral infection diagnosed in a community setting was also verified. Two methods were used to validate our panviral signature using microarray datasets derived from PBMC mRNA from a published study of viral respiratory infection ascertained from a cohort of pediatric patients with microbiologically proven influenza A infection with linked gene expression data. See, Ramilo et al., "Gene expression patterns in blood leukocytes discriminate patients with acute infections," Blood (2007) vol. 109, 2066-2077, incorporated herein by reference in its entirety.

Figure 5:
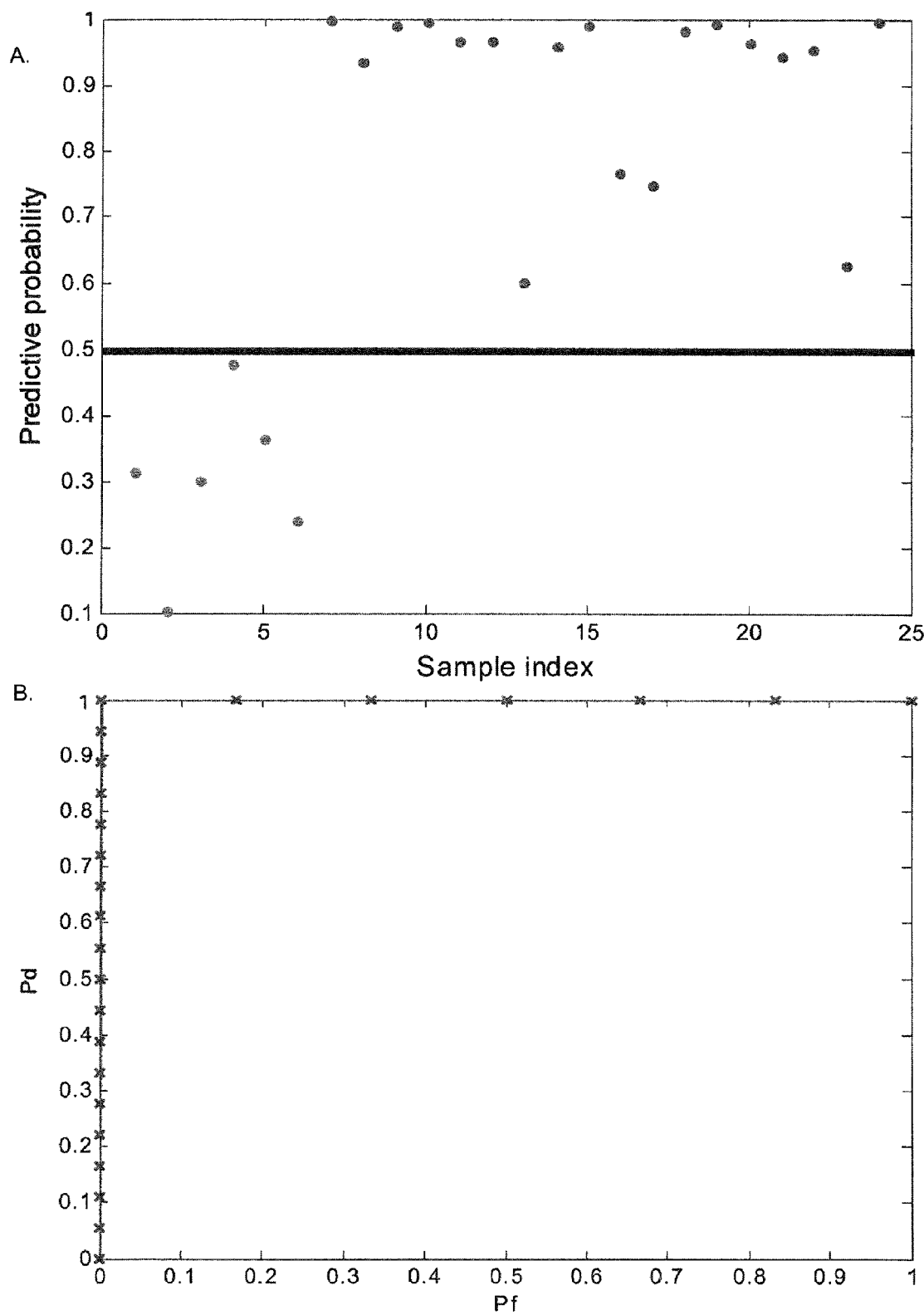
FIG. 5 shows that the panviral factor derived from the three experimental cohorts (rhinovirus, RSV, and influenza) predicts subjects with culture-proven influenza infection from an independent dataset with a high degree of accuracy.

First, the panviral classifier built on the combined three challenge datasets was used to predict disease state (uninfected versus influenza A infection) in the literature cohort (FIG. 5). Despite differences in subject ascertainment in the experimental cohort and the literature cohort [as well as other potential confounders (such as age and demographics)], the subjects were accurately classified as influenza A infected versus no infection in the literature cohort. This classification of subjects in the literature cohort was highly accurate [100% (23/23) for influenza infected versus no infection] (FIG. 5 B). Prediction of viral infection in a pre-existing dataset using genes identified as discriminative in an experimental dataset reinforces the robust nature of both the methodology and the classifier.

FIG. 5 shows that the panviral factor derived from the three experimental cohorts (rhinovirus, RSV, and influenza) predicts subjects with culture-proven influenza infection from an independent dataset with a high degree of accuracy. The panviral classifier built on the combined three challenge datasets was used to predict disease state (uninfected versus influenza A infection) in the literature cohort. FIG. 5 A) shows the predictive capability of the pan-viral factor to classify subjects with no infection (red) versus influenza A infection (blue). X-axis represents the individual subjects and y-axis represents the decision threshold. 0.5 is chosen as the threshold for generation of the subsequent ROC curves. FIG. 5 B) shows the prediction of influenza A infected versus healthy hospitalized control subjects using the pan-viral classifier.

Classification of subjects in the literature cohort was highly accurate [100% (23/23) for influenza infected versus no infection].

Figure 7:
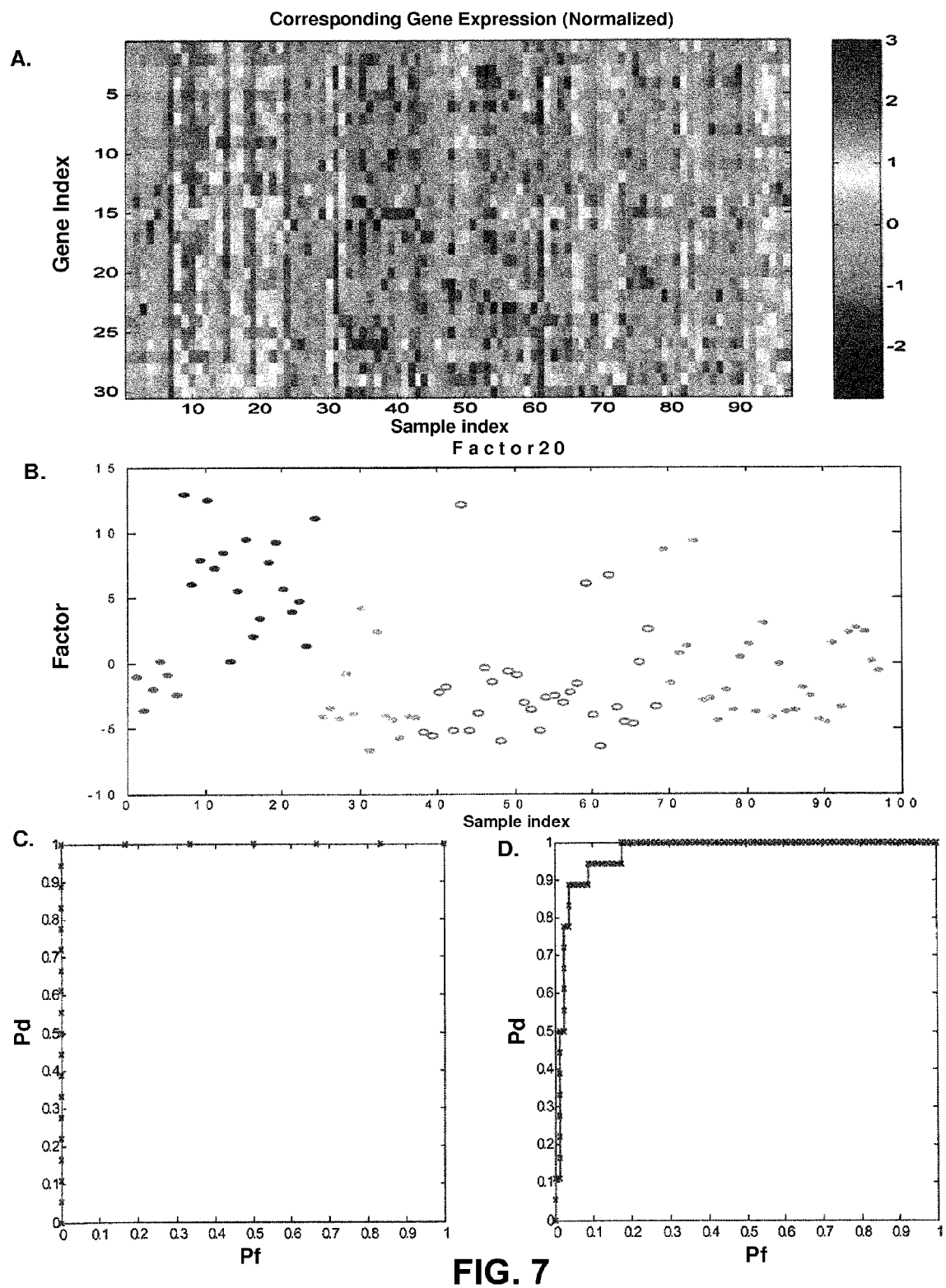
FIG. 7 shows the application of sparse latent factor regression analysis to an existing dataset of PBMC expression in microbiologically confirmed infections (influenza A, S. pneumoniae, S. aureus, and E. coli).

In the second approach, the raw gene expression data from the literature data set was re-analyzed using the same statistical methods that were utilized to generate the rhinovirus, RSV, and influenza expression signatures. Similar to the analysis of the rhinovirus-, RSV-, and influenza-infected cohorts, twenty factors were built using the entire gene set from all persons in the literature cohort (FIG. 7). These factors were used to build a classifier that distinguished persons with influenza A (n=18) from healthy controls (n=6 pediatric subjects hospitalized for elective surgery). The top 30 genes in this factor were used as features for the sparse probit regression model to perform leave-one-out cross validation and generate ROC curves to estimate performance of the algorithm. Leave-one-out cross validation correctly identified 100% of the 24 individuals in this dataset (FIG. 7 C). Of the 27 unique genes represented in the literature cohort factor, 20 were also present in the panviral factor derived from the experimental cohorts. Of the 28 unique genes represented in the panviral factor derived from our experimental cohorts, 20 were also present in the literature cohort factor. The probit function was also used to discriminate between influenza A infection and bacterial infection (FIG. 7 D), with cross-validation correctly classifying 90/97 subjects (misclassification rate 7%). This finding further supports the panviral factor derived above is a robust disease signature at time of peak symptoms.

Example 4

Figure 8:
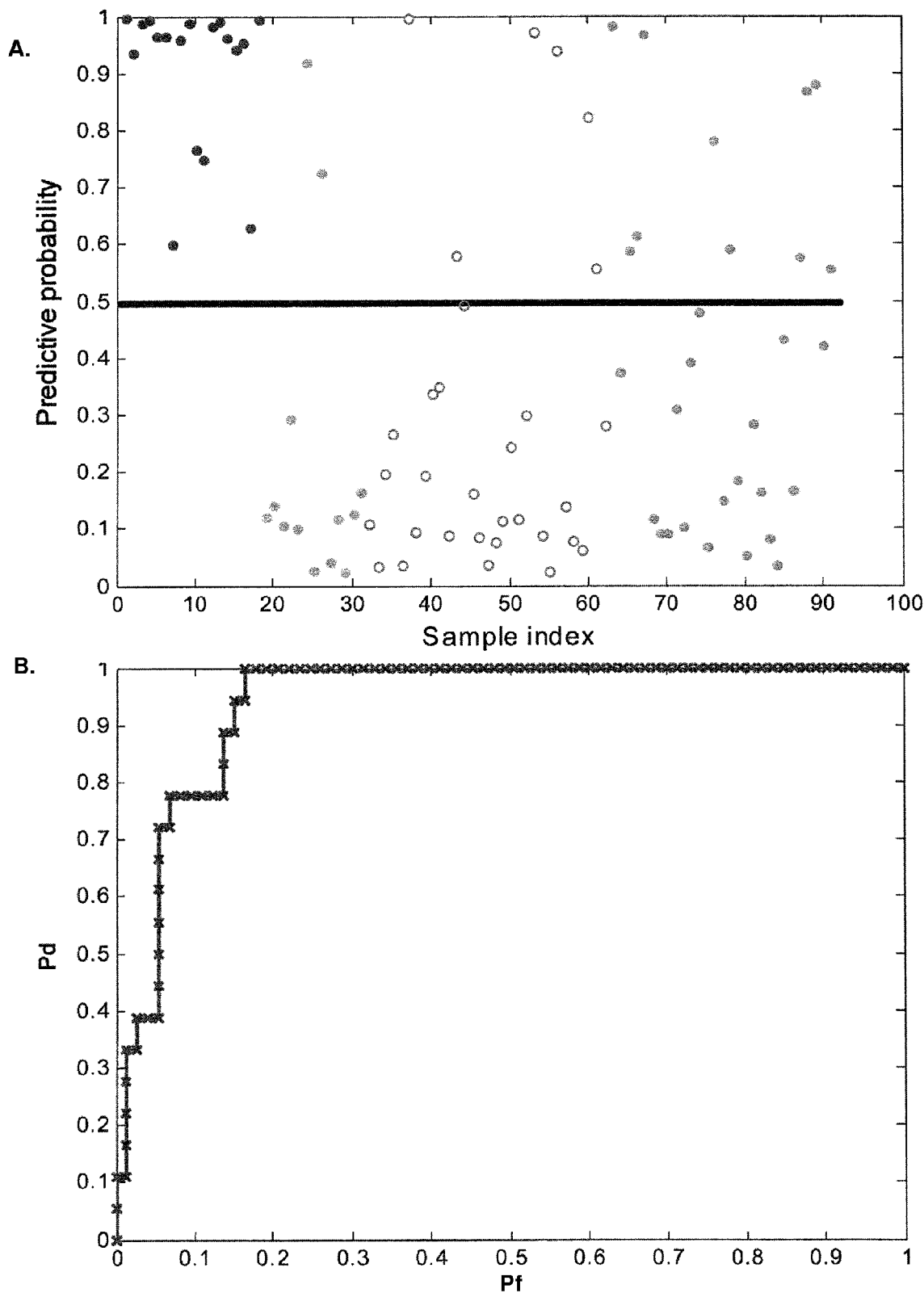
FIG. 8 shows that panviral factor derived from the three experimental cohorts (rhinovirus, RSV, and influenza) distinguishes subjects from an independent dataset with culture-proven influenza infection versus bacterial infection with a high degree of accuracy.

Identification of Viral Infection in Literature Cohort Having Bacterial Infections The specificity of the panviral gene expression factor for viral infections was also confirmed. We used microarray datasets available in the literature [14] derived from PBMC mRNA from a cohort of pediatric patients with microbiologically proven *S. pneumoniae, S. aureus,* or *E. coli* infections [(*S. pneumonia* (n=13), *S. aureus* (n=31), or *E. coli* (n=29)]. Similar to the analysis above, the panviral classifier built on the three combined challenge datasets was used to predict disease state (influenza A infection versus bacterial infection) in the literature cohort (FIG. 8). Classification of subjects in the literature cohort was highly accurate: 80% (73/91) for influenza infected versus any bacterial infection and 93% (31/33) for influenza infected versus pneumococcal infection. This analysis confirms specificity of the viral infection signature to discriminate not only between subjects with acute respiratory viral infection and uninfected subjects, but also from subjects with acute bacterial infections, including bacterial respiratory infection. Ultimately, the differentiation that is most valuable clinically may be discriminative between host response to viral respiratory tract infection and bacterial pneumonia (i.e. *S. pneumoniae* infection). Thus, despite inherent differences in sample acquisition and study design between the experimental rhinovirus, RSV, and influenza cohorts and the literature cohort, these analyses confirm the robust nature of gene expression signatures that differentiate subjects with respiratory viral infection from subjects with bacterial infections, including pneumococcal infection, and from healthy subjects.

PROPHETIC EXAMPLES

Example 5

Gene Expression Profiles for Respiratory Infection in Humans

A prospective study will be undertaken in which 200 healthy adult, male volunteers will be challenged sequentially with either RSV or placebo and monitored in a clinical research unit. The ages, ethnicities, and races of enrollees will match those of US war fighters, enabling assessment of relevant, inter-individual variability. Primary end-points will be four-fold or greater rise in RSV IgG antibody as measured by EIA. A secondary endpoint will be the development of coryzal symptoms and clinical signs of RSV infection.

Two hundred healthy male volunteers of an age (18-40 years) and ethnic background representative of US active military personnel will be challenged. Potential subjects will be tested for baseline serum titers of IgG to RSV F and G proteins using solid phase EIA. Based on previous data defining successful infection upon inoculation, patients with a titer $\leq 9.36$ log 2 will preferentially enrolled in a 3:1 ratio with patients with higher titers. The absence of ongoing RSV transmission will be determined by community laboratory surveillance. Subjects will be actively screened for asthma or hypersensitivity by spirometry and skin testing. Subjects will be screened for HIV, hepatitis B, and hepatitis C, as well as abnormal liver or renal function, immunosuppressive illness, or an acute respiratory illness or fever within 1 week of challenge. Subjects will also be excluded if they have close contact to high-risk persons including children less than 2 years of age or immunocompromised patients.

The challenge pool to be evaluated in this study will consist of RSV A2 (group A) prepared under GMP conditions by Walter Reed Army Institute of Research (WRAIR) under contract to NIAID. The final pool will contain a titer of 105 TCID50 per ml and will be assured free of adventitious pathogens. The protocol will include 0.5 cc of thawed A2 virus at 4.5 10g10 TCID50 in 25% sucrose (a 1:2 dilution) will be instilled into both nostrils in the recumbent position.

There will be little viral shedding in the first three days after inoculation, therefore, subjects will be followed as outpatients for 72 hours and then admitted to an isolation room in the clinical research facility for an additional 9 days. Subjects will maintain a diary card on which they will grade respiratory and systemic symptoms twice daily. Respiratory and systemic illness will be defined as two or more symptoms on two consecutive days. Oral temperature will also be recorded twice daily. A complete blood count (CBC) with differential and clinical chemistry tests, including liver function and serum creatinine, will be tested on day 12 and 28 after inoculation. Serial blood samples (PAXgene™ RNA tubes 5 cc, EDTA whole blood 5 cc, serum separator 5 cc) will be obtained with exhaled breath condensate daily for 12 days.

Host biomarker profiles will also be defined using a cohort of 30 persons with a viral challenge and a placebo challenge. This sample size has 90% power to detect at least a 2-fold change in expression levels in the 70% least variable genes with and alpha of 0.001 (ref. 28). Additional statistical methods will be used to evaluate global molecular expression patterns and characterize them into metagenes, or expression profile signatures that will be utilized to supplement the murine findings in Example 1. The focus will be on patterns evident in the data structure in order to minimize the need to compare human and murine responses on a gene-bygene or molecule-by-molecule basis. Utilizing a time course model, with evaluation of subjects on successive days following infection (early-presymptomatic through symptomatic), molecular expression signatures specific to infection, as well as elucidating the earliest potential time points for expression change identification, will be defined.

The study will show a greater than 90% efficacy in detecting RSV infection based upon host the biomarkers.

Example 6

Identifying Community-Acquired Acute Respiratory Disease Surveillance (CARDS) Among Military and College-Aged Cohorts The predictive models developed in the Examples above will be validated using two military-aged cohorts. Using sentinel cases of CARI of confirmed viral etiology (using rapid molecular diagnostic tests) in these two populations, a cohort of exposed contacts, a subset of whom will go on to develop symptomatic disease, will be identified. Using sentinel CARI cases of known viral etiology, an observational cohort of heavily exposed, but asymptomatic patients who may be incubating infection will also be identified and monitored prospectively. Using this cohort, the performance of the predictive models will be validated.

Surveillance for acute viral CARI will be performed in two high-risk populations of young adults, Duke University undergraduate students who live in dormitories and U.S. Army reservists currently stationed at Ft. Bragg in Fayetteville, N.C. Duke University is a major independent, coeducational university with approximately 11,000 students, 82% of whom live on campus in dormitory housing. Ft. Bragg, in Fayetteville, N.C., is a major US Army installation with over 50,000 persons on base.

A student or reservist will be eligible for enrollment as an index case if they present with 3 or more symptoms of acute respiratory illness (e.g., new onset cough or rhinorrhea, increase sputum production, pharyngitis, shortness of breath, chills, headache, myalgias, radiographic evidence of pneumonia) OR fever (T≥38.0) and two or more symptoms of acute respiratory illness OR a positive point-of-care rapid influenza test. In addition to their standard of care, a real-time multiplex PCR for diverse respiratory viral pathogens (influenza A and B, parainfluenza 1, 2, and 3, adenovirus, RSV, metapneumovirus, corona virus, and rhinovirus) developed specifically for this program will be used to confirm a patient's eligibility for enrollment as an index case, thus triggering the development of the contact cohort. Fifty PCR positive patients will be enrolled as sentinel cases from each site for a total of 100 sentinel events. A potential close contact (CC) will include all asymptomatic fellow students or reservists who share immediate living space OR shared common space OR are identified by the sentinel case as a close contact. Up to 10 CC per IC will be targeted for enrollment into the exposure cohort. Patients will be excluded if they are <18 years old or >40 years old, have signs or symptoms of acute respiratory illness, have an existing chronic medical condition, if they have recently been hospitalized or treated with antibiotic therapy for a different viral, bacterial, or fungal infection within 7 days of presentation, or if they are participating in an ongoing clinical trial. A confirmed case of respiratory viral infection for the CC cohort will be defined as respiratory symptoms (within 7 days of enrollment) and a 4-fold rise in IgG (at day 21) to the IC's PCR-positive virus. An investigator at each site will review the chief complaint for patients presenting to each clinic. The specific implementation of this surveillance will differ for each institution in order to minimize impact upon the usual flow of patients through the facility.

Baseline studies ($T_0$): Upon provision of informed consent, the student or reservist will be asked to provide answers to a standardized questionnaire including demographics, recent exposures and stressors, and symptoms. Each CC will have blood (15 cc-5 cc PAXgene™ RNA tube, 5 cc EDTA, 5 cc serum separator), urine, and an NP swab performed on the day of identification to assess if they have the IC virus present in the nasopharynx, their biomarker profile on the day of enrollment, and to assess their serologic antibody status to the viral infection of interest at baseline.

Each CC (~1000 persons) will be provided a symptom diary to record daily symptoms for 21 days. Each CC patient with a positive PCR concordant with the sentinel case viral etiology will have daily blood and urine samples obtained for the subsequent 7 days or until symptoms develop. Blood and urine specimens for biomarker profiling will continue daily until symptoms resolve, usually 48 to 72 hrs(42). Each CC with a negative baseline respiratory viral PCR will be monitored for symptoms. Should the patient become symptomatic, a repeat NP swab will be performed to determine viral etiology. A subset of PCR-negative CC in a ratio of 1:1 with PCR-positive patients will have their biomarker profile monitored at daily intervals for 7 days. At the completion of the 21 days, each enrolled CC will turn in their diary and will have a repeat blood, urine and NP swab performed to again assess for virus in the nasopharynx, biomarker profile, and serology for definitive assessment of infectious exposure.

This investigation will validate the accuracy of the clinicomolecular predictive model developed in EXAMPLE 1 for identifying the primary endpoint of patients exposed to a virus who will develop acute respiratory symptoms that may impede their ability to participate in military activities. For CARI screening for IC, it is estimated that a viral etiology will be detected in approximately 10-25% (30). For this reason, it is expected that between 400 to 1000 CARI (200-500/site) patients to identify our IC cohort. Among the CC cohort, it is estimated that concordant virus will be detected in 20% of the exposed persons (~200 persons) (43-48). Further, it is estimated that 50% of PCR-positive subjects will go on to develop symptomatic infection (100 persons). As the sensitivity of the PCR approaches 90%, an additional 11 patients from the PCR-negative subset of CC will go on to develop symptomatic confirmed infection. Therefore, it is estimated that 111 viral infections will be confirmed.

Data will be entered into an identical local relational database at Duke and Ft. Bragg. Patients and samples will be coded, the codes secured to ensure patient confidentiality, and patient identifiers will not be present in the database. The individual site data will be integrated together with biomarker candidate assay values, and the integrated database will be made available to the consortium. Following data analysis and publication of results, the database will be freely shared in accord with the stipulations of the RFA.

The active-learning techniques will be extended to a nonmyopic, cost-sensitive setting, using partially observable Markov decision processes (POMDPs). The POMDP will yield a policy for optimal presymptom diagnosis that will be tested. Imperfect sensitivity and specificity of diagnostic test methods for case determination inherently limits gene/metabolite/protein expression signature. For the clinical data contributing to the model there may be omission of presymptomatic information, heterogeneity in the patient population may limit generalizability and testing in multiple cohorts of varying ethnic backgrounds may be desirable.

Inclusion of a limited number of diagnoses in the initial prediction cohort will enhance the sensitivity and specificity of our findings. Enrollment of patients CARI or defined viral etiology may vary by time of year and the vagaries of respiratory disease outbreaks, necessitating the prolongation of the enrollment period.

Example 7

Screening Antiviral Targets Against Influenza

Twenty four healthy ferrets (Mustela furo) will have blood samples drawn and will be screened for factor 6 (influenza) gene levels according to the protocol described in EXAMPLE 1. The pre-inoculation levels will serve as the standard for each test subject, however a global standard will also be developed for the population of twenty four subjects. The 24 subjects will be divided into four groups of six. Two groups (A and B) of six test animals will not be inoculated with influenza. Group A will not be administered the antiviral agent, and will serve as a control. Group B will be administered the antiviral agent, and will act as control against increased gene expression due to the administration of the antiviral agent. Two groups (C and D) of six test animals will be inoculated with influenza. The twelve animals will develop influenza symptoms, approximately four days after inoculation. All 24 test animals will be screened for factor 6 expression at four days post-inoculation to verify increased expression of factor 6 in the test animals inoculated with influenza. Group C will not be administered the antiviral agent and will develop full influenza.

Following screening on day four post-inoculation, Groups B and D will be administered an amount of the antiviral agent. All 24 test animals will again be screened at six days post-inoculation. Group A will show no change in expression levels between four and six days post-inoculation. Group B will show no change in expression levels between four and six days post-inoculation. Group D will show reduced expression of factor 6 at six days post-inoculation compared to four days post-inoculation. Group C will show increased expression of factor 6 between four and six days post-inoculation. Group D expression will be smaller than Group C expression at six days post-inoculation. The study will, thus, verify that the antiviral agent is effective against influenza in ferrets.

Thus, the invention provides, among other things, methods for identifying infectious disease and assays for identifying infectious disease. Various features and advantages of the invention are set forth in the following claims.

The invention claimed is:

1. A method of identifying a subject infected with a respiratory virus comprising:

a) determining gene expression levels of panviral signature genes from a peripheral blood cell sample of the subject, wherein the panviral signature genes consist of ATF3, CXCL10, DDX58, HERC5, IFI27, IFI44, IFI44L, IFI6, IFIT1, IFIT2, IFIT3, ISG15, LAMP3, LOC26010, LOC727996, LY6E, MX1, OAS1, OAS2, OAS3, OASL, PML, RSAD2, RTP4, SEPT4, SERPING1, SIGLEC1, TNFAIP6, and XAF1, wherein determining comprises a method selected from the group consisting of assaying the sample with an array comprising a plurality of nucleic acid oligomers, real time PCR, assaying the sample with an array comprising a plurality of antibodies, and LC/MS;

b) comparing the gene expression levels of the panviral signature genes of step a) to standard gene expression levels for the panviral signature genes, wherein a difference between the levels of expression of the panviral signature genes and the standard gene expression levels is indicative of a subject infected with a respiratory virus; and c) administering an effective amount of an anti-viral therapeutic agent to the subject.

2. The method of claim 1, wherein the respiratory virus is rhinovirus.

3. The method of claim 1, wherein the respiratory virus is respiratory syncytial virus.

4. The method of claim 1, wherein the respiratory virus is influenza.

5. The method of claim 1, wherein genetic material from the peripheral blood sample is isolated and amplified prior to determining gene expression levels.

6. A method of identifying a type of viral respiratory infection, the method comprising:

a) determining gene expression levels of genes from a peripheral blood cell sample of the subject, wherein determining gene expression levels comprises a method selected from the group consisting of assaying the sample with an array comprising a plurality of nucleic acid oligomers, real time PCR, assaying the sample with an array comprising a plurality of antibodies, and LC/MS, wherein:

i) the genes consists of RSAD2, LAMP3, IFI44L, IFIT1, SIGLEC1, IFI44, OAS3, LOC727996, SERPING1, HERC5, ISG15, IFI6, INDO, MX1, IFIT3, OASL, LOC26010, OASL, CXCL10, ATF3, OAS1, DDX58, OAS1, LY6E, OAS2, CCL2, XAF1, IFIT2, and SOCS1 and the viral respiratory infection is rhinovirus infection;

ii) the genes consists of RSAD2, SERPING1, IFI44L, IFIT1, IFI44, LAMP3, OAS3, HERC5, ISG15, IFIT3, SIGLEC1, OASL, OAS1, LOC26010, MX1, IFI6, FCGR1A, GBP1, ATF3, IFIT5, LAP3, OASL, IFIT2, RTP4, GBP1, DDX58, ETV7, FCGR1B, and OAS1 and the viral respiratory infection is respiratory syncytial virus infection; or iii) the genes consists of RSAD2, IFI44L, SIGLEC1, LAMP3, IFIT1, IFI44, SERPING1, IFI27, ISG15, HERC5, LOC26010, IFI6, LOC727996, IFIT3, OAS3, OASL, SEPT4, XAF1, OAS1, LY6E, MS4A4A, SIGLEC1, TNFAIP6, CCL2, OAS1, MX1, TNFAIP6, RTP4, and OASL and the viral respiratory infection is influenza infection;

b) comparing the gene expression levels of genes of step a) to standard gene expression levels, wherein a difference between the levels of expression of the genes and the standard gene expression levels is indicative of a subject infected with a viral respiratory infection; and c) administering an effective amount of an anti-viral therapeutic agent to the subject.

7. A method of distinguishing between a viral respiratory infection and a bacterial respiratory infection in a subject comprising:

a) determining gene expression levels of panviral signature genes from a peripheral blood cell sample of the subject, wherein the panviral signature genes consist of ATF3, CXCL10, DDX58, HERC5, IFI27, IFI44, IFI44L, IFI6, IFIT1, IFIT2, IFIT3, ISG15, LAMP3, LOC26010, LOC727996, LY6E, MX1, OAS1, OAS2, OAS3, OASL, PML, RSAD2, RTP4, SEPT4, SERPING1, SIGLEC1, TNFAIP6, and XAF1, wherein determining gene expression levels comprises a method selected from the group consisting of assaying the sample with an array comprising a plurality of nucleic acid oligomers, real time PCR, assaying the sample with an array comprising a plurality of antibodies, and LC/MS;

b) comparing the gene expression levels of the panviral signature genes of step a) to standard gene expression levels for the panviral signature genes, wherein a difference between the levels of expression of the panviral signature genes and the standard gene expression levels is indicative of a subject infected with a respiratory virus, and c) administering an effective amount of an anti-viral therapeutic agent to the subject.

8. The method of claim 1, wherein the expression levels of each of the panviral signature genes in the peripheral blood cell sample are normalized and wherein the normalized expression levels are used as features for a sparse probit regression model to predict infection status.

9. The method of claim 8, wherein a predictive probability greater than 0.5 indicates that the subject is infected with a respiratory virus.

10. The method of claim 6, wherein the expression levels of the genes are normalized and wherein the normalized expression levels are used as features for a sparse probit regression model to predict infection status.

11. The method of claim 7, wherein the expression levels of each of the panviral signature genes in the peripheral blood cell sample are normalized and wherein the normalized expression levels are used as features for a sparse probit regression model to predict infection status.

12. The method of claim 11, wherein a predictive probability greater than 0.5 indicates that the subject is infected with a respiratory virus.

* * * * *